(12) United States Patent
Sako et al.

(10) Patent No.: US 7,438,898 B1
(45) Date of Patent: Oct. 21, 2008

(54) HAIR CONDITIONING COMPOSITION COMPRISING CARBOXYLIC ACID/CARBOXYLATE COPOLYMER, AND VISIBLE PARTICLE

(75) Inventors: Takashi Sako, Kobe (JP); Bruce Russell Cox, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/744,269

(22) PCT Filed: Jul. 30, 1998

(86) PCT No.: PCT/US98/15853

§ 371 (c)(1),
(2), (4) Date: Jan. 22, 2001

(87) PCT Pub. No.: WO00/06089

PCT Pub. Date: Feb. 10, 2000

(51) Int. Cl.
*A61K 8/72* (2006.01)
*A61Q 5/00* (2006.01)
(52) U.S. Cl. .................... 424/70.11; 424/70.1; 424/401
(58) Field of Classification Search .............. 424/70.16, 424/70.12, 70.28, 70.1, 70.9, 74, 401, 70.11
See application file for complete search history.

(56) References Cited

U.S. PATENT DOCUMENTS

| | | | |
|---|---|---|---|
| 5,403,508 A * | 4/1995 | Reng et al. ................... | 510/119 |
| 5,429,820 A | 7/1995 | Kamitari | |
| 5,756,436 A | 5/1998 | Royce et al. | |
| 5,840,293 A | 11/1998 | Nacht et al. | |
| 5,993,792 A * | 11/1999 | Rath et al. ................ | 424/70.28 |
| 6,004,545 A * | 12/1999 | Karlen et al. ............ | 424/70.12 |
| 6,106,816 A * | 8/2000 | Hitchen ................... | 424/70.16 |

FOREIGN PATENT DOCUMENTS

| | | |
|---|---|---|
| GB | 1471406 | 4/1977 |
| JP | 06080559 A | 3/1994 |
| KR | WO-97/23194 * | 7/1997 |
| WO | WO 93/07862 | 4/1993 |
| WO | WO-94/12151 A1 | 6/1994 |
| WO | WO 9735543 | 10/1997 |

* cited by examiner

*Primary Examiner*—Johann Richter
*Assistant Examiner*—Danielle Sullivan
(74) *Attorney, Agent, or Firm*—Andrew A. Paul; Linda M. Sivik; Marianne Dressman

(57) ABSTRACT

Hair conditioning compositions are disclosed comprising: (1) a carboxylic acid/carboxylate copolymer; (2) a visible particle; and (3) an aqueous carrier.

11 Claims, No Drawings

HAIR CONDITIONING COMPOSITION COMPRISING CARBOXYLIC ACID/CARBOXYLATE COPOLYMER, AND VISIBLE PARTICLE

TECHNICAL FIELD

The present invention relates to hair conditioning compositions comprising an carboxylic acid/carboxylate copolymer and a visible particle.

BACKGROUND

Human hair becomes soiled due to its contact with the surrounding environment and from sebum secreted by the scalp. The soiling of the hair causes it to have a dirty or greasy feel, and an unattractive appearance. The soiling of the hair necessitates shampooing with regularity.

Shampooing cleans the hair by removing excess soil and sebum. However, shampooing can leave the hair in a wet, tangled, and generally unmanageable state. Once the hair dries, it is often left in a dry, rough, lusterless, or frizzy condition due to removal of the hair's natural oils and other natural conditioning and moisturizing components. The hair can further be left with increased levels of static upon drying which can interfere with combing and result in a condition commonly referred to as "fly-away hair", or contribute to an undesirable phenomena of "split ends", particularly for long hair.

A variety of approaches have been developed to alleviate these after-shampoo problems. These approaches range from post-shampoo application of hair conditioner such as leave-on and rinse-off products, to hair conditioning shampoos which attempt to both cleanse and condition the hair from a single product. Although some consumers prefer the ease and convenience of a shampoo which includes conditioners, a substantial proportion of consumers prefer the more conventional conditioner formulations which are applied to the hair as a separate step from shampooing, usually subsequent to shampooing. Such consumers who prefer the conventional conditioner formulations value the relatively higher conditioning effect, or convenience of changing the amount of conditioning depending on the condition of hair or portion of hair.

Conditioning formulations can be in the form of rinse-off products or leave-on products, and can be in the form of an emulsion, cream, gel, spray, and mousse. Products in the form of cream, gel, and mousse are suitable in that the consumer can easily control the amount and distribution of the product. As such, these products are particularly suitable for leave-on products.

Leave-on products having aesthetic advantages are preferred by the consumer. Transparent or nearly transparent products including distinct visible particles are particularly preferred with regard to aesthetics. To deliver a product having such aesthetics in a stable product, a polymeric material capable of providing a suitable viscosity to suspend the visible particles is necessary. However, conventional leave-on products are not completely satisfactory in providing such aesthetic effects while delivering good feel on the hair and hands upon usage.

Based on the foregoing, there remains a desire to provide hair conditioning compositions suitable for leave-on use which provide favorable aesthetic benefits, are easy to apply on the hair, and leave the hair and hands with a clean feeling.

None of the existing art provides all of the advantages and benefits of the present invention.

SUMMARY

The present invention is directed to a hair conditioning composition comprising:

(1) an carboxylic acid/carboxylate copolymer;

(2) a visible particle; and (3) an aqueous carrier.

These and other features, aspects, and advantages of the present invention will become evident to those skilled in the art from a reading of the present disclosure.

DETAILED DESCRIPTION

While the specification concludes with claims which particularly point out and distinctly claim the invention, it is believed the present invention will be better understood from the following description.

All cited references are incorporated herein by reference in their entireties. Citation of any reference is not an admission regarding any determination as to its availability as prior art to the claimed invention.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

The aspects and embodiments of the present invention set forth in this document have many advantages. For example, the hair conditioning compositions of the present invention provide: favorable aesthetic benefits, and leave the hair and hands with a clean feeling. In one embodiment of the present invention, a transparent hair conditioning composition can be provided.

Carboxylic Acid/Carboxylate Copolymer

The compositions of the present invention comprise an carboxylic acid/carboxylate copolymer. The carboxylic acid/carboxylate copolymers herein are hydrophobically-modified cross-linked copolymers of carboxylic acid and alkyl carboxylate, and have an amphiphilic property. These carboxylic acid/carboxylate copolymers are obtained by copolymerizing 1) a carboxylic acid monomer such as acrylic acid, methacrylic acid, maleic acid, maleic anhydride, itaconic acid, fumaric acid, crotonic acid, or α-chloroacrylic acid, 2) a carboxylic ester having an alkyl chain of from 1 to about 30 carbons, and preferably 3) a crosslinking agent of the following formula:

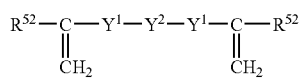

wherein $R^{52}$ is a hydrogen or an alkyl group having from about 1 to about 30 carbons; $Y^1$, independently, is oxygen, $CH_2O$, COO, OCO,

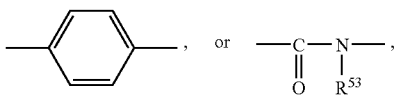

wherein $R^{53}$ is a hydrogen or an alkyl group having from about 1 to about 30 carbons; and $Y^2$ is selected from $(CH_2)_{m'''}$, $(CH_2CH_2O)_{m'''}$, or $(CH_2CH_2CH_2O)_{m'''}$ wherein $m''$ is an integer of from 1 to about 30. The carboxylic acid/carboxylate copolymers herein are believed to provide appropriate viscosity and rheology properties to the composition, and to emulsify and stabilize certain conditioning agents in the composition. It is further believed that, because of the alkyl group contained in the copolymer, the carboxylic acid/carboxylate copolymers do not make the composition undesirably sticky.

The composition of the present invention preferably comprises the carboxylic acid/carboxylate copolymer at a level by weight of from about 0.01% to about 10%, more preferably from about 0.1% to about 2%.

Suitable carboxylic acid/carboxylate copolymers herein are acrylic acid/alkyl acrylate copolymers having the following formula:

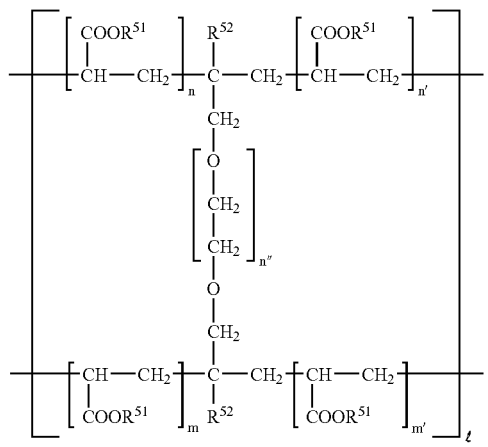

wherein $R^{51}$, independently, is a hydrogen or an alkyl of 1 to 30 carbons wherein at least one of $R^{51}$ is a hydrogen, $R^{52}$ is defined above, n, n', m and m' are integers in which n+n'+m+m' is from about 40 to about 100, n'' is an integer of from 1 to about 30, and $\ell$ is defined so that the copolymer has a molecular weight of about 500,000 to about 3,000,000.

Commercially available carboxylic acid/carboxylate copolymers useful herein include: CTFA name Acrylates/C10-30 Alkyl Acrylate Crosspolymer having tradenames Pemulen TR-1, Pemulen TR-2, Carbopol 1342, Carbopol 1382, and Carbopol ETD 2020, all available from B. F. Goodrich Company.

Neutralizing agents may be included to neutralize the carboxylic acid/carboxylate copolymers herein. Nonlimiting examples of such neutralizing agents include sodium hydroxide, potssium hydroxide, ammonium hydroxide, monethanolamine, diethanolamine, triethanolamine, diisopropanolamine, aminomethylpropanol, tromethamine, tetrahydroxypropyl ethylenediamine, and mixtures thereof.

Visible Particle

The compositions of the present invention may further comprise a visible particle. By definition, a visible particle is a particle which can be distinctively detected as an individual particle by the naked eye when comprised in the present composition, and which is stable in the present composition. The visible particle can be of any size, shape, or color, according to the desired characteristic of the product, so long as it is distinctively detected as an individual particle by the naked eye. Generally, the visible particle has an average diameter of from about 50 μm to about 3000 μm, preferably from about 100 μm to about 1000 μm, more preferably from about 300 μm to about 1000 μm. By stable, it is meant that the visible particles are not disintegrated, agglomerated, or separated under normal shelf conditions. In one preferred embodiment of the present invention, the composition is substantially transparent. In such an embodiment, the visible particles provide a highly suitable aesthetic benefit. What is generally meant by transparent, is that a black substance having the size of a 1 cm×1 cm square can be detected by the naked eye through 1 cm thickness of the present composition.

The visible particles herein are used at levels of from about 0.01% to about 5% by weight of the composition.

The visible particle herein comprises a structural material and preferably an encompassed material.

The structural material provides a certain strength to the visible particle so that they retain their distinctively detectable structure in the present composition under normal shelf conditions. In one preferred embodiment, the structural material further can be broken and disintegrated with very little shear on the hand with the fingers upon use.

Visible particles useful herein include capsules, shelled particles, beads, pellets, droplets, pills, caplets, tablets, grains, flakes, powders and granules. The visible particles can be solid or liquid, filled or un-filled, so long as they are stable in the present composition. The structural material used for making the visible particles varies depending on the compatibility with other components, as well as material, if any, to be encompassed in the visible particles. Exemplary materials for making the visible particles herein include: polysaccharide and saccharide derivatives such as crystalline cellulose, cellulose acetate, cellulose acetate butyrate, cellulose acetate phthalate, cellulose nitrate, ethylcellulose, hydroxypropylcellulose, hydroxypropylmethylcellulose, hydroxypropylmethylcellulose phthalate, methyl cellulose, sodium carboxymethylcellulose, gum acacia (gum arabic), agar, agarose, maltodextrin, sodium alginate, calcium alginate, dextran, starch, galactose, glucosamine, cyclodextrin, chitin, amylose, amylopectin, glycogen, laminaran, lichenan, curdlan, inulin, levan, pectin, mannan, xylan, alginic acid, arabic acid, glucommannan, agarose, agaropectin, prophyran, carrageenen, fucoidan, glycosaminoglycan, hyaluronic acid, chondroitin, peptidoglycan, lipopolysaccharide, guar gum, starch, and starch derivatives; oligosaccharides such as sucrose, lactose, maltose, uronic acid, muramic acid, cellobiose, isomaltose, planteose, melezitose, gentianose, maltotriose, stachyose, glucoside and polyglucoside; monosaccharides such as glucose, fructose, and mannose; synthetic polymers such as acrylic polymers and copolymers including polyacrylamide, poly(alkyl cyanoacrylate), and poly(ethylene-vinyl acetate), and carboxyvinyl polymer, polyamide, poly(methyl vinyl ether-maleic anhydride), poly(adipyl-L-lysine), polycarbonate, polyterephthalamide, polyvinyl acetate phthalate, poly(terephthaloyl-L-lysine), polyarylsulfone, poly(methylmethacrylate), poly(ϵ-caprolactone), polyvinylpyrrolidone, polydimethylsiloxane, polyoxyethylene, polyester, polyglycolic acid, polylactic acid, polyglutamic acid, polylysine, polystyrene, poly(styrene-acrylonitrile), polyimide, and poly(vinyl alcohol); and other material such as fat, fatty acid, fatty alcohol, milk solids, molasses, gelatin, gluten, albumin, shellac, caseinate, bees wax, carnauba wax, spermaceti wax, hydrogenated tallow, glycerol monopalmitate, glycerol dipalmitate, hydrogenated castor oil, glycerol monostearate, glycerol distearate, glycerol tristearate, 12-hydroxystearyl alcohol, protein, and protein derivatives; and mixtures thereof. Components herein may be described in other sections as useful components for the present composition. The components herein, however, are substantially used to make the structure of the visible particles, and are not dissolved or dispersed in the bulk of the present composition under normal shelf conditions.

Highly preferable structural material herein comprises components selected from the group consisting of polysaccharides and their derivatives, saccharides and their derivatives, oligosaccharides, monosaccharides, and mixtures thereof, still preferably, components from the above mentioned group wherein components having various water solubility are selected. In a particularly preferred embodiment, the structural material is made of components selected from the group consisting of cellulose, cellulose derivatives, saccharides, and mixtures thereof.

The visible particle herein may encompass, contain, or be filled with an encompassed material. Such encompassed material can be water soluble or water insoluble, and comprise components such as: vitamins, amino acids, proteins and protein derivatives, herbal extracts, pigments, dyes, antimicrobial agents, chelating agents, UV absorbers, optical brighteners, silicone compounds, perfumes, humectants which are generally water soluble, additional conditioning agents which are generally water insoluble, and mixtures thereof. In one embodiment, water soluble components are preferred encompassed material. In another embodiment, components selected from the group consisting of vitamins, amino acids, proteins, protein derivatives, herbal extracts, and mixtures thereof are preferred encompassed material. In yet another embodiment, components selected from the group consisting of vitamin E, pantothenyl ethyl ether, panthenol, *Polygonum multiflori* extracts, and mixtures thereof are preferred encompassed material.

Vitamins and amino acids useful as encompassed material herein include: water soluble vitamins such as vitamin B1, B2, B6, B12, C, pantothenic acid, pantothenyl ethyl ether, panthenol, biotin, and their derivatives, water soluble amino acids such as asparagine, alanin, indole, glutamic acid and their salts, water insoluble vitamins such as vitamin A, D, E, and their derivatives, water insoluble amino acids such as tyrosine, tryptamine, and their salts.

Pigments useful as encompassed material herein include inorganic, nitroso, monoazo, disazo, carotenoid, triphenyl methan, triaryl methane, xanthene, quinoline, oxazine, azine, anthraquinone, indigoid, thionindigoid, quinacridone, phthalocianine, botanical, natural colors, including: water soluble components such as those having C. I. Names: Acid Red 18, 26, 27, 33, 51, 52, 87, 88, 92, 94, 95, Acid Yellow 1, 3, 11, 23, 36, 40, 73, Food Yellow 3, Food Green 3, Food blue 2, Food Red 1, 6, Acid Blue 5, 9, 74, Pigment Red 57-1, 53(Na), Basic Violet 10, Solvent Red 49, Acid orange 7, 20, 24, Acid Green 1, 3, 5, 25, Solvent Green 7, Acid Violet 9, 43; water insoluble components such as those having C. I. Names: Pigment Red 53(Ba), 49(Na), 49(Ca), 49(Ba), 49(Sr), 57, Solvent Red 23, 24, 43, 48, 72, 73, Solvent Orange 2, 7, Pigment Red 4, 24, 48, 63(Ca)$_3$, 64, Vat Red 1, Vat blue 1, 6, Pigment Orange 1, 5, 13, Solvent Yellow 5, 6, 33, Pigment Yellow 1, 12, Solvent Green 3, Solvent Violet 13, Solvent Blue 63, Pigment Blue 15, titanium dioxides, chlorophyllin copper complex, ultramarines, aluminum powder, bentonite, calcium carbonate, barium sulfate, bismuthine, calcium sulfate, carbon black, bone black, chromic acid, cobalt blue, gold, ferric oxides, hydrated ferric oxide, ferric ferrocyanide, magnesium carbonate, manganous phosphate, silver, and zinc oxides.

Antimicrobial agents useful as encompassed material include those useful as cosmetic biocides and antidandruff agents including: water soluble components such as piroctone olamine, water insoluble components such as 3,4,4'-trichlorocarbanilide (trichlosan), triclocarban and zinc pyrithione.

Chelating agents useful as encompassed material include: 2,2'-dipyridylamine; 1,10-phenanthroline {o-phenanthroline}; di-2-pyridyl ketone; 2,3-bis(2-pyridyl)pyrazine; 2,3-bis(2-pyridyl)-5,6-dihydropyrazine; 1,1'-carbonyldiimidazole; 2,4-bis(5,6-diphenyl-1,2,4-triazine-3-yl)pyridine; 2,4,6-tri(2-pyridyl)-1,3,5-triazine; 4,4'-dimethyl-2,2'dipyridyl; 2,2'-biquinoline; di-2-pyridyl glyoxal {2,2'-pyridil}; 2-(2-pyridyl)benzimidazole; 2,2'-bipyrazine; 3-(2-pyridyl)5,6-diphenyl-1,2,4-trazine; 3-(4-phenyl-2-pyridyl)-5-phenyl-1,2,4-triazine; 3-(4-phenyl-2-pyridyl)-5,6-diphenyl-1,2,4-triazine; 2,3,5,6-tetrakis-(2'-pyridyl)-pyrazine; 2,6-pyridinedicarboxylic acid; 2,4,5-trihydroxypyrimidine; phenyl 2-pyridyl ketoxime; 3-amino-5,6-dimethyl-1,2,4-triazine; 6-hydroxy-2-phenyl-3(2H)-pyridazinone; 2,4-pteridinediol {lumazine}; 2,2-dipyridyl; and 2,3-dihydroxypyridine.

Useful silicone compounds, humectants, additional conditioning agents, UV absorbers, optical brighteners, and herbal extracts for encompassed material are the same as those exemplified in other portions of the specification. The components herein, however, are substantially retained within the breakable visible particles, and are substantially not dissolved in the bulk of the present composition under normal shelf conditions.

Particularly useful commercially available visible particles herein are those with tradenames Unisphere and Unicerin available from Induchem AG (Switzerland), and Confetti Dermal Essentials available from United-Guardian Inc. (NY, USA). Unisphere and Unicerin particles are made of microcrystalline cellulose, hydroxypropyl cellulose, lactose, vitamins, pigments, and proteins. Upon use, the Unisphere and Unicerin particles can be disintegrated with very little shear on the hand with the fingers with practically no resistance, and readily dissolve in the composition.

Aqueous Carrier

The compositions of the present invention comprise an aqueous carrier. The level and species of the carrier are selected according to the compatibility with other components, and other desired characteristic of the product.

Carriers useful in the present invention include water and water solutions of lower alkyl alcohols. Lower alkyl alcohols useful herein are monohydric alcohols having 1 to 6 carbons, more preferably ethanol and isopropanol.

Preferably, the aqueous carrier is substantially water. Deionized water is preferably used. Water from natural sources including mineral cations can also be used, depending on the desired characteristic of the product. Generally, the compositions of the present invention comprise from about 20% to about 99%, preferably from about 40% to about 98%, and more preferably from about 50% to about 98% water.

The pH of the present composition is preferably from about 4 to about 9, more preferably from about 4.5 to about 7.5. Buffers and other pH adjusting agents can be included to achieve the desirable pH.

Amphoteric Conditioning Polymer

The compositions of the present invention may further comprise an amphoteric conditioning polymer.

The amphoteric conditioning polymers herein are those compatible with the carboxylic acid/carboxylate copolymers and which provide conditioning benefit to the hair. Although some of the amphoteric conditioning polymers herein may have some hair holding or hair fixative properties, such hair holding or hair fixative properties are not a requirement for the amphoteric conditioning polymers herein. The amphoteric conditioning polymers useful herein are those including at least one cationic monomer and at least one anionic monomer; the cationic monomer being quaternary ammonium, preferably dialkyl diallyl ammonium chloride or carboxylamidoalkyl trialkyl ammonium chloride; and the anionic monomer being carboxylic acid. The amphoteric conditioning polymers herein may include nonionic monomers such as acrylamine, methacrylate, or ethacrylate. Further, the amphoteric conditioning polymers useful herein do not contain betanized monomers.

The composition of the present invention preferably comprises the amphoteric conditioning polymer at a level by weight of from about 0.01% to about 10%, more preferably from about 0.1% to about 5%.

Useful herein are polymers with the CTFA name Polyquaternium 22, Polyquaternium 39, and Polyquaternium 47. Such polymers are, for example, copolymers consisting of dimethyldiallyl ammonium chloride and acrylic acid, terpolymers consisting of dimethyldiallyl ammonium chloride and acrylamide, and terpolymers consisting of acrylic acid methacrylamidopropyl trimethylammonium chloride and methyl acrylate such as those of the following formula wherein the ratio of $n^6:n^7:n^8$ is 45:45:10:

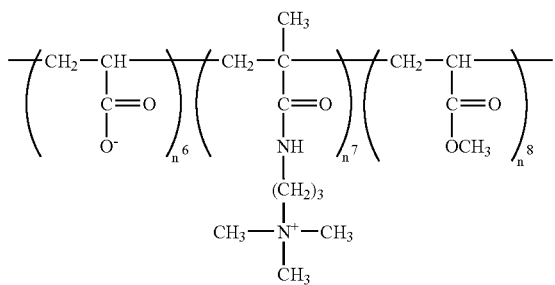

Highly preferred commercially available amphoteric conditioning polymers herein include Polyquaternium 22 with tradenames MERQUAT 280, MERQUAT 295, Polyquaternium 39 with tradenames MERQUAT PLUS 3330, MERQUAT PLUS 3331, and Polyquaternium 47 with tradenames MERQUAT 2001, MERQUAT 2001N, all available from Calgon Corporation.

Also useful herein are polymers resulting from the copolymerisation of a vinyl monomer carrying at least one carboxyl group, such as acrylic acid, methacrylic acid, maleic acid, itaconic acid, fumaric acid, crotonic acid, or alphachloroacrylic acid, and a basic monomer which is a substituted vinyl compound containing at least one basic nitrogen atom, such as dialkylaminoalkyl methacrylates and acrylates and dialkylaminoalkylmethacrylamides and acrylamides.

Also useful herein are polymers containing units derived from:
i) at least one monomer chosen from among acrylamides or methacrylamides substituted on the nitrogen by an alkyl radical,
ii) at least one acid comonomer containing one or more reactive carboxyl groups, and
iii) at least one basic comonomer, such as esters, with primary, secondary and tertiary amine substituents and quaternary ammonium substituents, of acrylic and methacrylic acids, and the product resulting from the quaternisation of dimethylaminoethyl methacrylate with dimethyl or diethyl sulfate.

The N-substituted acrylamides or methacrylamides which are most particularly preferred are the groups in which the alkyl radicals contain from 2 to 12 carbon atoms, especially N-ethylacrylamide, N-tert.-butylacrylamide, N-tert.-octylacrylamide, N-octylacrylamide, N-decylacrylamide and N-dodecylacrylamide and also the corresponding methacrylamides. The acid comonomers are chosen more particularly from amongst acrylic, methacrylic, crotonic, itaconic, maleic and fumaric acids and also the alkyl monoesters of maleic acid or fumaric acid in which alkyl has 1 to 4 carbon atoms.

The preferred basic comonomers are aminoethyl, butylaminoethyl, N,N'-dimethylaminoethyl and N-tert.-butylaminoethyl methacrylates.

Commercially available amphoteric conditioning polymers herein include octylacrylamine/acrylates/butylaminoethyl methoacrylate copolymers with the tradenames AMPHOMER, AMPHOMER SH701, AMPHOMER 28-4910, AMPHOMER LV71, and AMPHOMER LV47 supplied by National Starch & Chemical.

Humectant

The compositions of the present invention may further comprise a humectant. The humectants herein are selected from the group consisting of polyhydric alcohols, water soluble alkoxylated nonionic polymers, and mixtures thereof. The humectants herein are preferably used at levels by weight of the composition of from about 0.1% to about 20%, more preferably from about 0.5% to about 5%.

Polyhydric alcohols useful herein include glycerin, sorbitol, propylene glycol, butylene glycol, hexylene glycol, ethoxylated glucose, 1,2-hexane diol, hexanetriol, dipropylene glycol, erythritol, trehalose, diglycerin, xylitol, maltitol, maltose, glucose, fructose, sodium chondroitin sulfate, sodium hyaluronate, sodium adenosin phosphate, sodium lactate, pyrrolidone carbonate, glucosamine, cyclodextrin, and mixtures thereof.

Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof.

Commercially available humectants herein include: glycerin with tradenames STAR and SUPEROL available from The Procter & Gamble Company, CRODEROL GA7000 available from Croda Universal Ltd., PRECERIN series available from Unichema, and a same tradename as the chemical name available from NOF; propylene glycol with tradename LEXOL PG-865/855 available from Inolex, 1,2-PROPYLENE GLYCOL USP available from BASF; sorbitol with tradenames LIPONIC series available from Lipo, SORBO, ALEX, A-625, and A-641 available from ICI, and UNISWEET 70, UNISWEET CONC available from UPI; dipropylene glycol with the same tradename available from BASF; diglycerin with tradename DIGLYCEROL available from Solvay GmbH; xylitol with the same tradename available from Kyowa and Eizai; maltitol with tradename MALBIT available from Hayashibara, sodium chondroitin sulfate with the same tradename available from Freeman and Bioiberica, and with tradename ATOMERGIC SODIUM CHONDROITIN SULFATE available from Atomergic Chemetals; sodium hyaluronate with tradenames ACTIMOIST available from Active Organics, AVIAN SODIUM HYALURONATE series available from Intergen, HYALURONIC ACID Na available from Ichimaru Pharcos; sodium adenosin phophate with the same tradename available from Asahikasei, Kyowa, and Daiichi Seiyaku; sodium lactate with the same tradename available from Merck, Wako, and Showa Kako, cyclodextrin with tradenames CAVITRON available from American Maize, RHODOCAP series available from Rhone-Poulenc, and DEXPEARL available from Tomen; and polyethylene glycols with the tradename CARBOWAX series available from Union Carbide.

Silicone Compound

The compositions of the present invention may further comprise a silicone compound. The silicone compounds useful herein include volatile soluble or insoluble, or nonvolatile soluble or insoluble silicone conditioning agents. By soluble what is meant is that the silicone compound is miscible with the carrier of the composition so as to form part of the same phase. By insoluble what is meant is that the silicone forms a separate, discontinuous phase from the carrier, such as in the form of an emulsion or a suspension of droplets of the silicone. The silicone compounds herein may be made by any suitable method known in the art, including emulsion polymerization. The silicone compounds may further be incorporated in the present composition in the form of an emulsion, wherein the emulsion is made my mechanical mixing, or in the stage of synthesis through emulsion polymerization, with or without the aid of a surfactant selected from anionic surfactants, nonionic surfactants, cationic surfactants, and mixtures thereof.

The silicone compounds for use herein will preferably have a viscosity of from about 1,000 to about 2,000,000 centistokes at 25° C., more preferably from about 10,000 to about 1,800,000, and even more preferably from about 100,000 to about 1,500,000. The viscosity can be measured by means of a glass capillary viscometer as set forth in Dow Corning Corporate Test Method CTM0004, Jul. 20, 1970. Silicone compound of high molecular weight may be made by emulsion polymerization. Suitable silicone fluids include polyalkyl siloxanes, polyaryl siloxanes, polyalkylaryl siloxanes, polyether siloxane copolymers, and mixtures thereof. Other nonvolatile silicone compounds having hair conditioning properties can also be used.

The silicone compounds herein are preferably used at levels by weight of the composition of from about 0.1% to about 60%, more preferably from about 0.1% to about 40%.

The silicone compounds herein also include polyalkyl or polyaryl siloxanes with the following structure (I)

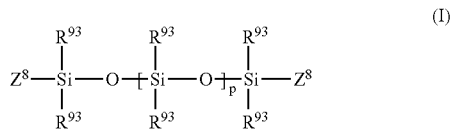

wherein $R^{93}$ is alkyl or aryl, and x is an integer from about 7 to about 8,000. $Z^8$ represents groups which block the ends of the silicone chains. The alkyl or aryl groups substituted on the siloxane chain ($R^{93}$) or at the ends of the siloxane chains $Z^8$ can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. Suitable $Z^8$ groups include hydroxy, methyl, methoxy, ethoxy, propoxy, and aryloxy. The two $R^{93}$ groups on the silicon atom may represent the same group or different groups. Preferably, the two $R^{93}$ groups represent the same group. Suitable $R^{93}$ groups include methyl, ethyl, propyl, phenyl, methylphenyl and phenylmethyl. The preferred silicone compounds are polydimethylsiloxane, polydiethylsiloxane, and polymethylphenylsiloxane. Polydimethylsiloxane, which is also known as dimethicone, is especially preferred. The polyalkylsiloxanes that can be used include, for example, polydimethylsiloxanes. These silicone compounds are available, for example, from the General Electric Company in their Viscasil® and SF 96 series, and from Dow Corning in their Dow Corning 200 series.

Polyalkylaryl siloxane fluids can also be used and include, for example, polymethylphenylsiloxanes. These siloxanes are available, for example, from the General Electric Company as SF 1075 methyl phenyl fluid or from Dow Corning as 556 Cosmetic Grade Fluid.

Especially preferred, for enhancing the shine characteristics of hair, are highly arylated silicone compounds, such as highly phenylated polyethyl silicone having refractive index of about 1.46 or higher, especially about 1.52 or higher. When these high refractive index silicone compounds are used, they should be mixed with a spreading agent, such as a surfactant or a silicone resin, as described below to decrease the surface tension and enhance the film forming ability of the material.

The silicone compounds that can be used include, for example, a polypropylene oxide modified polydimethylsiloxane although ethylene oxide or mixtures of ethylene oxide and propylene oxide can also be used. The ethylene oxide and polypropylene oxide level should be sufficiently low so as not to interfere with the dispersibility characteristics of the silicone. These material are also known as dimethicone copolyols.

Other silicone compounds include amino substituted materials. Suitable alkylamino substituted silicone compounds include those represented by the following structure (II)

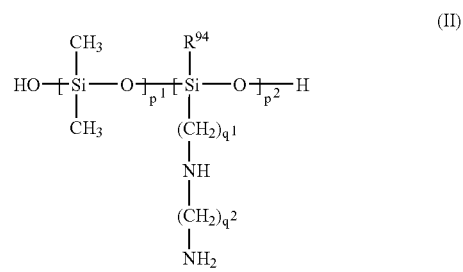

wherein $R^{94}$ is H, $CH_3$ or OH, $p^1$, $p^2$, $q^1$ and $q^2$ are integers which depend on the molecular weight, the average molecular weight being approximately between 5,000 and 10,000. This polymer is also known as "amodimethicone".

Suitable amino substituted silicone fluids include those represented by the formula (III)

in which G is chosen from the group consisting of hydrogen, phenyl, OH, $C_1$-$C_8$ alkyl and preferably methyl; a denotes 0 or an integer from 1 to 3, and preferably equals 0; b denotes 0 or 1 and preferably equals 1; the sum $p^3+p^4$ is a number from 1 to 2,000 and preferably from 50 to 150, $p^3$ being able to denote a number from 0 to 1,999 and preferably from 49 to 149 and $p^4$ being able to denote an integer from 1 to 2,000 and preferably from 1 to 10; $R^{97}$ is a monovalent radical of formula $C_{q3}H_{2q3}L$ in which q is an integer from 2 to 8 and L is chosen from the groups —N($R^{96}$)$CH_2$—$CH_2$—N($R^{96}$)$_2$
—N($R^{96}$)$_2$
—N($R^{96}$)$_3$X'
—N($R^{96}$)$CH_2$—$CH_2$—$NR^{96}H_2$X' in which $R^{96}$ is chosen from the group consisting of hydrogen, phenyl, benzyl, a saturated hydrocarbon radical, preferably an alkyl radical containing from 1 to 20 carbon atoms, and X' denotes a halide ion.

An especially preferred amino substituted silicone corresponding to formula (II) is the polymer known as "trimethylsilylamodimethicone" wherein $R^{94}$ is $CH_3$.

Other amino substituted silicone polymers which can be used are represented by the formula (V):

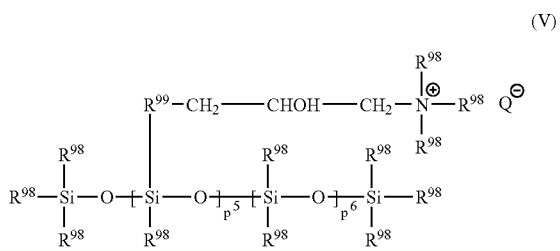

where $R^{98}$ denotes a monovalent hydrocarbon radical having from 1 to 18 carbon atoms, preferably an alkyl or alkenyl radical such as methyl; $R^{99}$ denotes a hydrocarbon radical, preferably a $C_1$-$C_{18}$ alkylene radical or a $C_1$-$C_{18}$, and more preferably $C_1$-$C_8$, alkyleneoxy radical; $Q^-$ is a halide ion, preferably chloride; $p^5$ denotes an average statistical value from 2 to 20, preferably from 2 to 8; $p^6$ denotes an average statistical value from 20 to 200, and preferably from 20 to 50. A preferred polymer of this class is available from Union Carbide under the name "UCAR SILICONE ALE 56."

References disclosing suitable nonvolatile dispersed silicone compounds include U.S. Pat. No. 2,826,551, to Geen; U.S. Pat. No. 3,964,500, to Drakoff, issued Jun. 22, 1976; U.S. Pat. No. 4,364,837, to Pader; and British Patent No. 849,433, to Woolston. "Silicon Compounds" distributed by Petrarch Systems, Inc., 1984, provides an extensive, though not exclusive, listing of suitable silicone compounds.

Another nonvolatile dispersed silicone that can be especially useful is a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicone compounds. This overlap is not intended as a limitation on any of these materials. Silicone gums are described by Petrarch, and others including U.S. Pat. No. 4,152,416, to Spitzer et al., issued May 1, 1979 and Noll, Walter, Chemistry and Technology of Silicones, N.Y.: Academic Press 1968. Also describing silicone gums are General Electric Silicone Rubber Product Data Sheets SE 30, SE 33, SE 54 and SE 76. The "silicone gums" will typically have a mass molecular weight in excess of about 200,000, generally between about 200,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof.

Also useful are silicone resins, which are highly crosslinked polymeric siloxane systems. The crosslinking is introduced through the incorporation of tri-functional and tetra-functional silanes with mono-functional or di-functional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units, and hence, a sufficient level of crosslinking, such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinylchlorosilanes, and tetrachlorosilane, with the methyl substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art. Without being bound by theory, it is believed that the silicone resins can enhance deposition of other silicone compounds on the hair and can enhance the glossiness of hair with high refractive index volumes.

Other useful silicone resins are silicone resin powders such as the material given the CTFA designation polymethylsilsequioxane, which is commercially available as Tospearl™ from Toshiba Silicones.

The method of manufacturing these silicone compounds, can be found in Encyclopedia of Polymer Science and Engineering, Volume 15, Second Edition, pp. 204-308, John Wiley & Sons, Inc., 1989.

Silicone materials and silicone resins in particular, can conveniently be identified according to a shorthand nomenclature system well known to those skilled in the art as the "MDTQ" nomenclature. Under this system, the silicone is described according to the presence of various siloxane monomer units which make up the silicone. Briefly, the symbol M denotes the mono-functional unit $(CH_3)_3SiO_{0.5}$; D denotes the difunctional unit $(CH_3)_2SiO$; T denotes the trifunctional unit $(CH_3)SiO_{1.5}$; and Q denotes the quadric- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyl, amino, hydroxyl, and the like. The molar ratios of the various units, either in terms of subscripts to the symbols indicating the total number of each type of unit in the silicone, or an average thereof, or as specifically indicated ratios in combination with molecular weight, complete the description of the silicone material under the MDTQ system. Higher relative molar amounts of T, Q, T' and/or Q' to D, D', M and/or or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MQ and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

Particularly suitable silicone compounds herein are nonvolatile silicone oils having a molecular weight of from about 200,000 to about 600,000 such as Dimethicone, and Dimethiconol. These silicone compounds can be incorporated in the composition as silicone oils solutions; the silicone oils being volatile or non-volatile.

Commercially available silicone compounds which are useful herein include Dimethicone with tradename DC345 available from Dow Corning Corporation, Dimethicone gum solutions with tradenames SE 30, SE 33, SE 54 and SE 76 available from General Electric, Dimethiconol with tradenames DCQ2-1403 and DCQ2-1401 available from Dow Corning Corporation, and emulsion polymerized Dimethiconol available from Toshiba Silicone as described in GB application 2,303,857.

Additional Viscosity Modifier

The compositions of the present invention may further comprise an additional viscosity modifier. The additional viscosity modifiers herein are water soluble or water miscible polymers, have the ability to increase the viscosity of the composition, and are compatible with the carboxylic acid/carboxylate copolymers. The additional viscosity modifier is selected so that the composition of the present composition has a suitable viscosity, preferably from about 1,000 cps to about 100,000 cps, more preferably from about 2,000 cps to about 50,000 cps. If such a viscosity is achieved without the additional viscosity modifier, the additional viscosity modifier may not be necessary. The viscosity herein can be suitably measured by Brookfield RVT at 20 rpm at 20° C. using either spindle #4, 5, 6 or 7 depending on the viscosity and the characteristic of the composition. The additional viscosity modifiers herein are preferably used at levels by weight of the composition of from about 0.001% to about 5%, more preferably from about 0.05% to about 3%.

Additional viscosity modifiers useful herein include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carragheenin, pectin, agar, quince seed (Cydonia oblonga mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid.

Polyalkylene glycols having a molecular weight of more than about 1000 are useful herein. Useful are those having the following general formula:

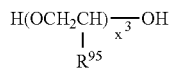

wherein $R^{95}$ is selected from the group consisting of H, methyl, and mixtures thereof. When $R^{95}$ is H, these materials are polymers of ethylene oxide, which are also known as polyethylene oxides, polyoxyethylenes, and polyethylene glycols. When $R^{95}$ is methyl, these materials are polymers of propylene oxide, which are also known as polypropylene oxides, polyoxypropylenes, and polypropylene glycols. When $R^{95}$ is methyl, it is also understood that various positional isomers of the resulting polymers can exist. In the above structure, x3 has an average value of from about 1500 to about 25,000, preferably from about 2500 to about 20,000, and more preferably from about 3500 to about 15,000. Other useful polymers include the polypropylene glycols and mixed polyethylene-polypropylene glycols, or polyoxyethylene-polyoxypropylene copolymer polymers. Polyethylene glycol polymers useful herein are PEG-2M wherein $R^{95}$ equals H and x3 has an average value of about 2,000 (PEG-2M is also known as Polyox WSR® N-10, which is available from Union Carbide and as PEG-2,000); PEG-5M wherein $R^{95}$ equals H and x3 has an average value of about 5,000 (PEG-5M is also known as Polyox WSR® N-35 and Polyox WSR® N-80, both available from Union Carbide and as PEG-5,000 and Polyethylene Glycol 300,000); PEG-7M wherein $R^{95}$ equals H and x3 has an average value of about 7,000 (PEG-7M is also known as Polyox WSR® N-750 available from Union Carbide); PEG-9M wherein $R^{95}$ equals H and x3 has an average value of about 9,000 (PEG 9-M is also known as Polyox WSR® N-3333 available from Union Carbide); and PEG-14 M wherein $R^{95}$ equals H and x3 has an average value of about 14,000 (PEG-14M is also known as Polyox WSR® N-3000 available from Union Carbide).

Commercially available additional viscosity modifiers highly useful herein include Carbomers with tradenames Carbopol 934, Carbopol 940, Carbopol 950, Carbopol 980, and Carbopol 981, all available from B. F. Goodrich Company, acrylates/steareth-20 methacrylate copolymer with tradename ACRYSOL 22 available from Rohm and Hass, nonoxynyl hydroxyethylcellulose with tradename AMERCELL POLYMER HM-1500 available from Amerchol, methylcellulose with tradename BENECEL, hydroxyethyl cellulose with tradename NATROSOL, hydroxypropyl cellulose with tradename KLUCEL, cetyl hydroxyethyl cellulose with tradename POLYSURF 67, all supplied by Herculus, ethylene oxide and/or propylene oxide based polymers with tradenames CARBOWAX PEGS, POLYOX WASRs, and UCON FLUIDS, all supplied by Amerchol.

UV Absorber

The compositions of the present invention may further comprise a UV (ultraviolet) absorber. UV absorbers are particularly useful for compositions of the present invention which are substantially transparent. The UV absorbers herein are preferably used at levels by weight of the composition of from about 0.01% to about 10%.

UV absorbers useful herein can be water soluble or water insoluble, including: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, benzyl, menthyl, glyceryl, and dipropyleneglycol esters); cinnamic acid derivatives (menthyl and benzyl esters, -phenyl cinnamonitrile; butyl cinnamoyl pyruvate; trihydroxycinnamic acid derivatives (esculetin, methylesculetin, daphnetin, and the glucosides, esculin and daphnin); dibenzalacetone and benzalacetophenone; naphtholsulfonates (sodium salts of 2-naphthol-3,6-disulfonic and of 2-naphtol-6,8-disulfonic acids); dihydroxy-naphthoic acid and its sals; o- and p-Hydroxybiphenyldisulfonates; quinine salts (bisulfate, sulfate, chloride, oleate, and tannate); quinoline derivatives (8-hydroxyquinoline salts, 2-phenylquinoline); hydroxy- or methoxy-substituted benzophenones; uric and vilouric acids; tannic acid and its derivatives (e.g., hexaethylether); (butyl carbityl) (6-propyl piperonyl)ether; hydroquinone; benzophenones (oxybenzene, sulisobenzone, dioxybenzone, benzooresorcinol, 2,2',4,4'-Tetrahydroxybenzophenone, 2,2'-Dihydroxy-4,4'-dimethoxybenzophenone, octabenzone); 4-Isopropyldibenzoylmethane; butylmethoxydibenzoylmethane; etocrylene; and 4-isopropyl-di-benzoylmethane. Of these, 2-ethylhexyl p-methoxycinnamate, 4,4'-t-butyl methoxydibenzoylmethane, 2-hydroxy-4- methoxybenzophenone, octyldimethyl p-aminobenzoic acid, digalloyltrioleate, 2,2-dihydroxy-4-methoxybenzophenone ethyl 4-[bis(hydroxypropyl)]aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethyl-aminobenzoic acid or aminobenzoate, 2-ethylhexyl p-dimethylamino-benzoate, 2-phenylbenzimidazole-5-sulfonic acid, 2-(p-dimethylaminophenyl)-5-sulfonicbenzoxazoic acid and mixtures thereof. Preferred sunscreens useful in the compositions of the present invention are 2-ethylhexyl p-methoxycinnamate, butyl-methoxydibenzoylmethane, 2-hydroxy-4-methoxybenzophenone, octyldimethyl p-aminobenzoic acid and mixtures thereof.

Optical Brightener

The compositions of the present invention may further comprise an optical brightener. Optical brighteners are compounds which absorb ultraviolet light and re-emit the energy in the form of visible light. Specifically, the optical brighteners useful herein have an absorption, preferably a major absorption peak, between a wavelength of about 1 nm and about 420 nm, and an emission, preferably a major emission peak, between a wavelength of about 360 nm and about 830 nm; wherein the major absorption peak has a shorter wavelength than the major emission peak. More preferably, the optical brighteners useful herein have a major absorption peak between a wavelength of about 200 nm and about 420 nm, and a major emission peak between a wavelength of about 400 nm and about 780 nm. Optical brighteners may or may not have minor absorption peaks in the visible range between a wavelength of about 360 nm and about 830 nm. Optical brighteners can be described by other names in the art and in other industries, such as fluorescent whitening agents, fluorescent brighteners, and fluorescent dyes.

When applied to hair via suitable vehicles, optical brighteners herein provide benefits to the hair in three areas. First, optical brighteners herein alter the color of the hair by emitting light in the visible range. Second, optical brighteners herein enhance the shine of the hair by emitting light in the visible range. Third, optical brighteners herein protect the hair from ultraviolet light by absorbing ultraviolet light.

Optical brighteners in general are based on the structures of aromatic and heteroaromatic systems which provide these unique characteristics. The optical brighteners useful in the present invention can be water soluble and water insoluble, and can be classified according to their base structures, as described hereafter. Preferable optical brighteners herein include polystyrylstilbenes, triazinstilbenes, hydroxycoumarins, aminocoumarins, triazoles, pyrazolines, oxazoles, pyrenes, porphyrins, and imidazoles.

The optical brighteners useful herein are preferably used at levels by weight of the composition of from about 0.001% to about 10%.

Polystyrylstilbenes

Polystyrylstilbenes are a class of compounds having two or more of the following base structure:

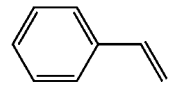

Polystyrylstilbenes useful in the present invention include those having formulae (1), (2) and (3):

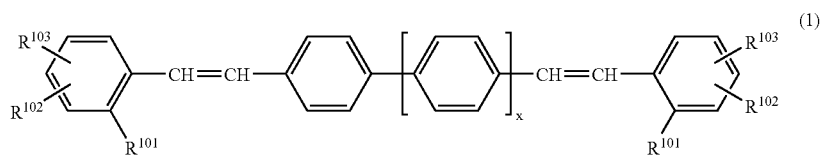

wherein $R^{101}$ is H, OH, $SO_3M$, COOM, $OSO_3M$, OPO(OH) OM, wherein M is H, Na, K, Ca, Mg, ammonium, mono-, di-, tri- or tetra-$C_1$-$C_{30}$-alkylammonium, mono-, di- or tri-$C_1$-$C_{30}$-hydroxyalkylammonium or ammonium that is di- or tri-substituted with by a mixture of $C_1$-$C_{30}$-alkyl and $C_1$-$C_{30}$-hydroxyalkyl groups; or $SO_2N(C_1$-$C_{30}$-alkyl$)_2$, O—(—$C_1$-$C_{30}$-alkyl), CN, Cl, COO($C_1$-$C_{30}$-alkyl), CON($C_1$-$C_{30}$-alkyl$)_2$ or O(CH$_2$)$_3$N$^+$(CH$_3$)$_2$X$^-$ wherein X$^-$ is an anion of a chloride, bromide, iodide, formate, acetate, propionate, glycolate, lactate, acrylate, methanephosphonate, phosphite, dimethyl or diethyl phosphite anion; CN, or alkyl of 1 to 30 carbons, $R^{102}$ and $R^{103}$, independently, are H, $SO_3M$ wherein M is as previously defined; and x is 0 or 1; wherein the compound has a trans-coplanar orientation or cis-coplanar orientation; preferably x is 1, $R^{101}$ is $SO_3Na$ and $R^{102}$ and $R^{103}$ are H; wherein the compound has a trans-coplanar orientation;

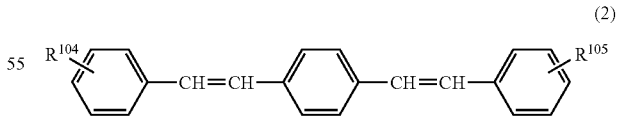

wherein $R^{104}$ and $R^{105}$, independently, are CN, COO($C_1$-$C_{30}$-alkyl), CONHC$_1$-$C_4$-alkyl, or CON($C_1$-$C_4$-alkyl)$_2$, wherein the compound has a trans-coplanar orientation or cis-coplanar orientation; preferably $R^{104}$ and $R^{105}$ is 2-cyano, wherein the compound has a trans-coplanar orientation; and

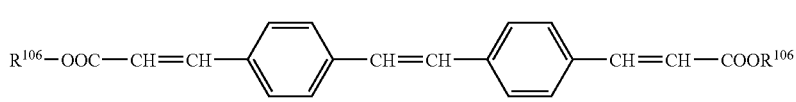

(3)

wherein each $R^{106}$, independently, is H, or alkyl of 1 to 30 carbons; and wherein the compound has a trans-coplanar orientation or cis-coplanar orientation, preferably a trans-coplanar orientation.

Suitable polystyryistilbenes include disodium-1,4'-bis(2-sulfostyryl) bisphenyl (C.I. Fluorescent Brightener 351) with tradename Tinopal CBS-X available from Ciba Specialty Chemicals, 1,4-bis(2-cyanostyryl)benzene (C.I. Fluorescent Brightener 199) with tradename Ultraphor RN available from BASF.

Triazinstilbenes

Triazinstilbenes are a class of compounds having both triazin and stilbene structures in the same molecule.

Triazinstilbenes useful in the present invention include those having formulae (4):

(4)

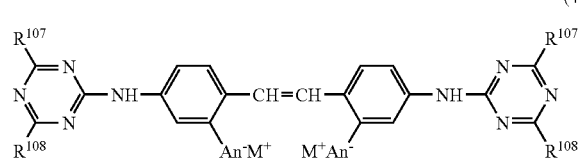

wherein $R^{107}$ and $R^{108}$, independently, are phenylamino, mono- or disulfonated phenylamino, morpholino, $N(CH_2CH_2OH)_2$, $N(CH_3)(CH_2CH_2OH)$, $NH_2$, $N(C_1$-$C_4$-alkyl$)_2$, $OCH_3$, Cl, $NH$—$(CH_2)_{1-4}SO_3H$ or $NH$—$(CH_2)_{1-4}OH$; $An^-$ is an anion of a carboxylate, sulfate, sulfonate, or phosphate, and M is as previously defined, wherein the compound has a trans-coplanar orientation or cis-coplanar orientation; preferably $R^{107}$ is 2,5-disulfophenylamino and each $R^{108}$ is morpholino; or each $R^{107}$ is 2,5-disulfophenylamino and each $R^{108}$ is $N(C_2H_5)_2$; or each $R^{107}$ is 3-sulfophenyl and each $R^{108}$ is $NH(CH_2CH_2OH)$ or $N(CH_2CH_2OH)_2$; or each $R^{107}$ is 4-sulfophenyl and each $R^{108}$ is $N(CH_2CH_2OH)_2$; and in each case, the sulfo group is $SO_3M$ in which M is sodium; wherein the compound has a trans-coplanar orientation.

Suitable triazinstilbenes include 4,4'-bis-[(4-anilino-6-bis(2-hydroxyethyl)amino-1,3,5-triazin-2-yl)amino]stilbene-2,2'-disulfonic acid with tradename Tinopal UNPA-GX available from Ciba Specialty Chemicals, 4,4'-bis-[(4-anilino-6-morpholine-1,3,5-triazin-2-yl)amino]stilbene-2,2'-disodium sulfonate with tradename Tinopal AMS-GX available from Ciba Specialty Chemicals, 4,4'-bis-[(4-anilino-6-(2-hydroxyethyl)methyl amino-1,3,5-triazin-2-yl)amino]stilbene-2,2'-disodium sulfonate with tradename Tinopal 5BM-GX available from Ciba Specialty Chemicals, 4'4-bis-[(4,6-dianilino-1,3,5-triazin-2-yl)amino]stilbene-2,2'-disodium sulfonate, 4,4'-bis-[(4-anilino-6-methylamino-1,3,5-triazin-2-yl)amino]stilbene-2,2'-disodium sulfonate, 4,4'-bis-[(4-anilino-6-ethylamino-1,3,5-triazin-2-yl)amino]stilbene-2,2'disodium sulfonate, and 4,4'-bis(4-phenyl-1,2,3-triazol-2-yl)stilbene-2,2'disulfonic acid.

Hydroxycoumarins

Hydroxycoumarins are a class of compounds having the following base coumarin structure and having at least one hydroxy moiety:

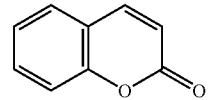

Hydroxycoumarins useful in the present invention include those having formulae (5):

(5)

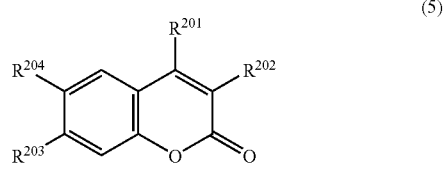

wherein $R^{201}$ is H, OH, Cl, $CH_3$, $CH_2COOH$, $CH_2SO_3H$, $CH_2OSO_3H$, or $CH_2OPO(OH)OH$, $R^{202}$ is H, phenyl, COO—$C_1$-$C_{30}$-alkyl, glucose, or a group of formula (6):

(6)

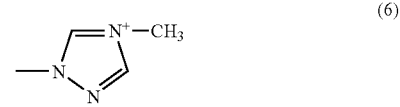

and $R^{203}$ is OH, or O—$C_1$-$C_{30}$-alkyl, and $R^{204}$ is OH or O—$C_1$-$C_{30}$ alkyl, glycoside, or a group of the following formula (7):

(7)

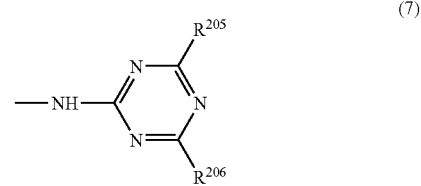

wherein $R^{205}$ and $R^{206}$ are independently, phenylamino, mono- or disulfonated phenylamino, morpholino, $N(CH_2CH_2OH)_2$, $N(CH_3)(CH_2CH_2OH)$, $NH_2$, $N(C_1$-$C_{30}$-alkyl$)_2$, $OCH_3$, Cl, $NH$—$(CH_2)_{14}SO_3H$ or $NH$—$(CH_2)_{1-4}OH$.

Suitable hydroxycoumarins include 6,7-dihydroxycoumarin available from Wako Chemicals, 4-methyl-7-hydroxycoumarin available from Wako Chemicals, 4-methyl-6,7-dihydroxycoumarin available from Wako Chemicals, esculin available from Wako Chemicals, and umbelliferone (4-hydroxycoumarin) available from Wako Chemicals.

Aminocoumarins

Aminocoumarins are a class of compounds having the base coumarin structure and having at least one amino moiety.

Aminocoumarins useful in the present inventions include those having formulae (8):

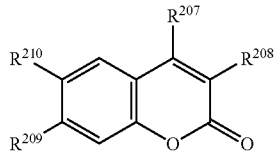

(8)

wherein $R^{207}$ is H, Cl, $CH_3$, $CH_2COOH$, $CH_2SO_3H$, $CH_2OSO_3H$, or $CH_2OPO(OH)OH$, $R^{208}$ is H, phenyl, or $COOC_1$-$C_{30}$ alkyl, and $R^{209}$ and $R^{210}$ are independently H, $NH_2$, $N(C_1$-$C_{30}$alkyl$)_2$, $NHC_1$-$C_{30}$alkyl, or $NHCOC_1$-$C_{30}$alkyl.

Suitable aminocoumarins include 4-methyl-7,7'-diethylamino coumarin with tradename Calcofluor-RWP available from BASF, 4-methyl-7,7'-dimethylamino coumarin with tradename Calcofluor-LD available from BASF.

Triazoles

Triazoles are a class of compounds having the following base structure:

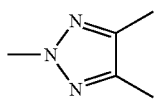

Triazoles useful in the present inventions include those having formulae (9) through (12) and (15) through (20):

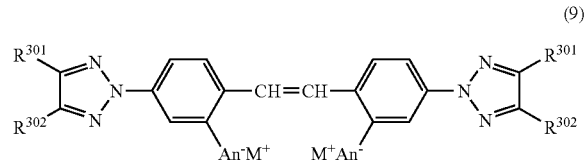

(9)

wherein $R^{301}$ and $R^{302}$, independently, are H, $C_1$-$C_{30}$alkyl, phenyl or monosulfonated phenyl; $An^-$ and M are as previously defined, wherein the compound has a trans-coplanar orientation or cis-coplanar orientation; preferably $R^{301}$ is phenyl, $R^{302}$ is H and M is sodium; wherein the compound has a trans-coplanar orientation;

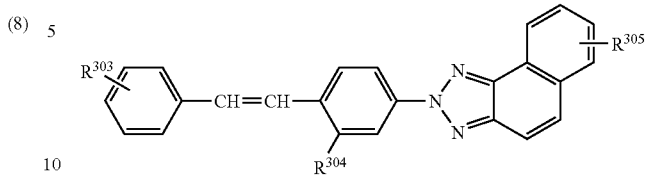

(10)

wherein $R^{303}$ is H or Cl; $R^{304}$ is $SO_3M$, $SO_2N(C_1$-$C_{30}$-alkyl$)_2$, $SO_2O$-phenyl or CN; $R^{305}$ is H, $SO_3M$, COOM, $OSO_3M$, or $OPO(OH)OM$; and M is as previously defined, wherein the compound has a trans-coplanar orientation or cis-coplanar orientation; preferably $R^{303}$ and $R^{305}$ are H and $R^{304}$ is $SO_3M$ in which M is Na; wherein the compound has a trans-coplanar orientation;

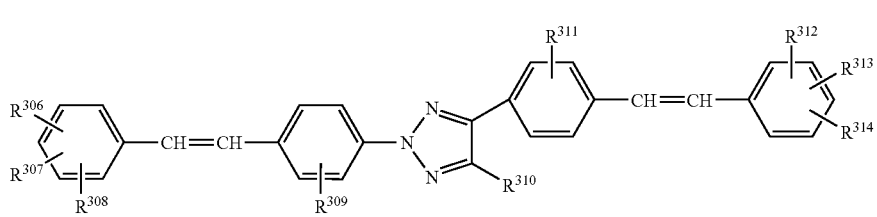

(11)

wherein each of $R^{306}$ and $R^{312}$ independently represents H, a sulfonic acid group or the salts, esters or amides thereof, a carboxylic acid group or the salts, esters or amides thereof, a cyano group, a halogen atom, an unsubstituted or substituted alkylsulfonyl, arylsulfonyl, alkyl, alkoxy, aralkyl, aryl, aryloxy, aralkoxy or cycloalkyl radical, an unsubstituted or substituted 5-membered heterocyclic ring containing 2 to 3 nitrogen atoms or one oxygen atom and 1 or 2 nitrogen atoms, or together with $R^{307}$ and $R^{313}$ they represent a methylenedioxy, ethylenedioxy, methylenoxymethylenoxy, trimethylene, tetramethylene, propenylene, butenylene or butadienylene radical, each of $R^{307}$ and $R^{313}$ independently represents H, a sulfonic acid group or the salts, esters or amides thereof, a carboxylic acid group or the salts, esters or amides thereof, a cyano group, a halogen atom, an unsubstituted or substituted alkyl or alkoxy radical, or together with $R^{306}$ and $R^{312}$ represent a methylenedioxy, ethylenedioxy, methylenoxymethylenoxy, trimethylene, tetramethylene, propenylene, butenylene or butadienylene radical, each of $R^{308}$ and $R^{314}$ independently represents H, a halogen atom or an unsubstituted or substituted alkyl radical, each of $R^{309}$ and $R^{311}$ independently represents H, a halogen atom, a cyano group a sulonic acid group or the salts, esters or amides thereof, or a carboxylic acid group or the salts, esters or amides thereof, and $R^{310}$ independently represents H, a halogen atom, a cyano group a sulfonic acid group or the salts, alkyl radicals preferably by hydroxy, alkoxy of 1 to 30 carbon atoms, cyano, halogen, carboxy, sulfonic acid groups, carbalkoxy having 1 to 30 carbon atoms in the alkoxy moiety, phenyl or phenoxy; alkoxy radicals can be substituted by hydroxy, alkoxy of 1 to 30 carbon atoms, cyano, halogen, carboxy, carbalkoxy having 1 to 30 carbon atoms in the alkoxy moiety, phenyl or phenoxy; phenyl, phenylalkyl or phenoxy radicals can be substituted by halogen, cyano, carboxy, carbalkoxy having 1 to 30 carbon atoms in the alkoxy moiety, sulfo, or alkyl or alkoxy each of 1 to 30 carbon atoms; wherein the compound has a trans-coplanar orientation or cis-coplanar orientation; possible cycloalkyl radicals are preferably cyclohexyl and cyclopentyl radicals which can be substituted by alkyl of 1 to 30 carbon atoms; possible 5-membered heterocyclic rings are v-triazole, oxazole or 1,3,4-oxdiazole radicals which can contain as substituents alkyl radicals of 1 to 4 carbon atoms, halogen, phenyl, carboxy, carbalkoxy having 1 to 30 carbon atoms in the alkoxy moiety, cyano, benzyl, alkoxy of 1 to 30 carbon atoms, phenoxy or sulfo, whilst two adjacent substituents of the triazole and oxazole radicals together are able to form a substituted or unsubstituted fused benzene nucleus; wherein the compound has a trans-coplanar orientation;

and wherein $R^{317}$ denotes H, alkyl with 1 to 30 carbon atoms, cyclohexyl, phenylalkyl with $C_1$-$C_{30}$ carbon atoms in the alkyl part, phenyl, alkoxy with 1 to 30 carbon atoms, or Cl, or, conjointly with $R^{318}$, denotes alkylene with 3 to 30 carbon atoms, $R^{318}$ denotes H or alkyl with 1 to 30 carbon atoms or, conjointly with $R^{317}$, denotes alkylene with 3 to 30 carbon atoms, $R^{319}$ denotes H or methyl, $R^{320}$ denotes H, alkyl with 1 to 30 carbon atoms, phenyl, alkoxy with 1 to 30 carbon atoms, or Cl, or, conjointly with $R^{321}$, denotes a fused benzene ring, $R^{321}$ denotes H or Cl or conjointly with $R^{320}$, denotes a fused benzene ring, $R^{315}$ denotes H, alkyl with 1 to 30 carbon atoms, alkoxy with 1 to 30 carbon atoms or Cl, $R^{316}$ denotes H or Cl, $Q^2$ denotes H, Cl alkyl with 1 to 30 carbon atoms or phenyl and $Q^3$ denotes H or Cl; wherein the compound has a trans-coplanar orientation or cis-coplanar orientation, preferably a trans-coplanar orientation;

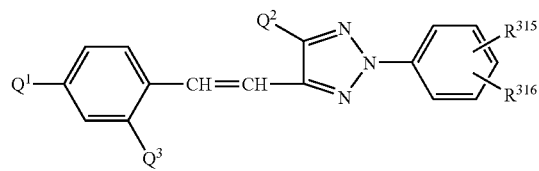
(12)

wherein $Q^1$ denotes one of the ring systems (13) or (14);

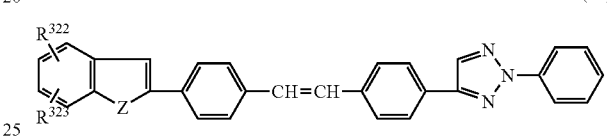
(15)

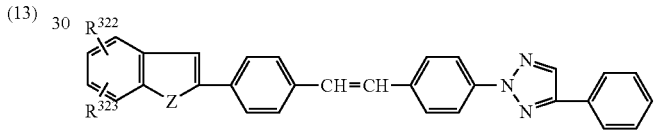
(16)

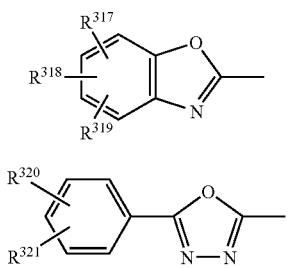
(13)
(14)

wherein $R^{322}$ denotes H, Cl, methyl, phenyl, benzyl, cyclohexyl or methoxy, $R^{323}$ denotes H or methyl and Z denotes O or S; wherein the compound has a trans-coplanar orientation or cis-coplanar orientation, preferably a trans-coplanar orientation; and

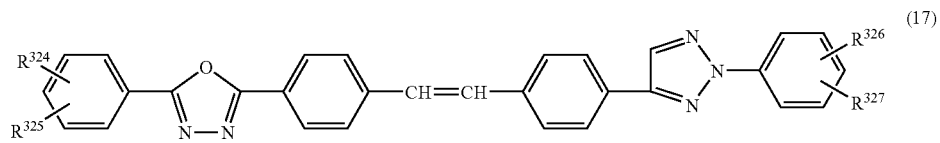
(17)

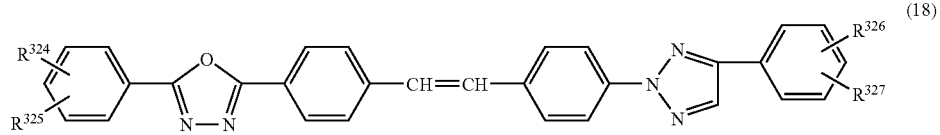
(18)

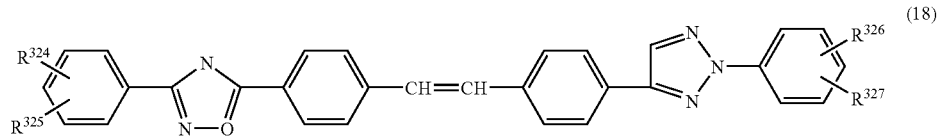
(18)

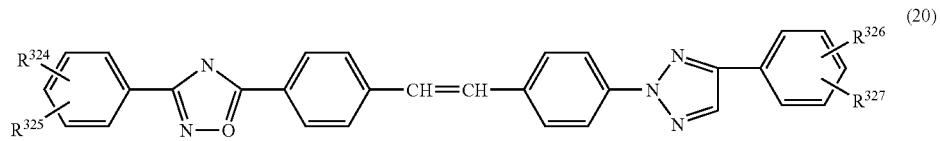
(20)

wherein $R^{324}$ denotes H, Cl, alkyl with 1 to 30 carbon atoms, phenylalkyl with 1 to 30 carbon atoms, phenyl or alkoxy with 1 to 30 carbon atoms, or $R^{324}$ conjointly with $R^{325}$ denotes a fused benzene radical, $R^{325}$ denotes H or methyl or $R^{325}$ conjointly with $R^{324}$ denotes a fused benzene radical, $R^{326}$ denotes H, alkyl with 1 to 30 carbon atoms, alkoxy with 1 to 30 carbon atoms, Cl, carbalkoxy with 1 to 30 carbon atoms or alkylsulfonyl with 1 to 30 carbon atoms and $R^{327}$ denotes H, Cl, methyl or methoxy; wherein the compound has a trans-coplanar orientation or cis-coplanar orientation, preferably a trans-coplanar orientation.

Suitable triazoles include 2-(4-styryl-3-sulfophenyl)-2H-naptho[1,2-d]triazole (C.I. Fluorescent Brightener 46) with tradename Tinopal RBS available from Ciba Specialty Chemicals.

Pyrazolines

Pyrazolines are a class of compounds having the following base structure:

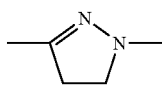

Pyrazolines useful in the present invention include those having formulae (21) through (23):

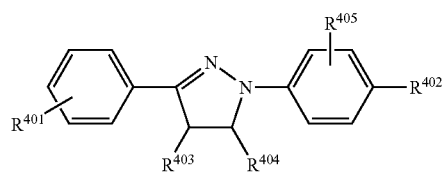
(21)

wherein $R^{401}$ is H, Cl or $N(C_1-C_{30}\text{-alkyl})_2$, $R^{402}$ is H, Cl, $SO_3M$, $SO_2NH_2$, $SO_2NH$—$(C_1-C_{30}\text{alkyl})$, COO—$C_1$-$C_{30}$alkyl, $SO_2$—$C_1$-$C_{30}$alkyl, $SO_2NH(CH_2)_{1-4}N^+(CH_3)_3$ or $SO_2(CH_2)_{1-4}N^+H(C_1-C_{30}\text{-alkyl})_2An^-$, $R^{403}$ and $R^{404}$ are the same or different and each is H, $C_1$-$C_{30}$alkyl or phenyl and $R^{405}$ is H or Cl; and $An^-$ and M are as previously defined, preferably $R^{401}$ is Cl, $R^{402}$ is $SO_2CH_2\,CH_2N^+H(C_1\text{-}C_4\text{-alkyl})_2An^-$ in which $An^-$ is phosphite and $R^{403}$, $R^{404}$ and $R^{405}$ are each H; and formulae (22) and (23) shown below.

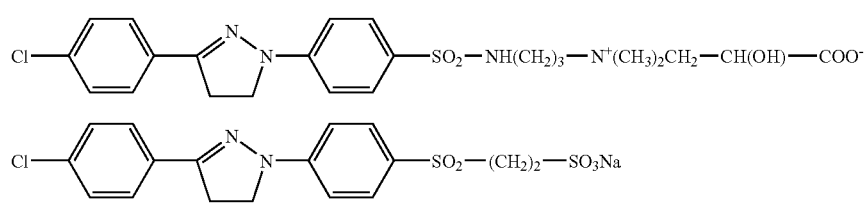

Suitable pyrazolines include 1-(4-amidosulfonylphenyl)-3-(4-chlorophenyl)-2-pyrazoline (C.I. Fluorescent Brightener 121) with tradename Blankophor DCB available from Bayer, 1-[4-(2-sulfoethylsulfonyl)phenyl]-3-(4-chlorophenyl)-2-pyrazoline, 1'-[4-(2-sulfoethylsulfonyl)phenyl]-3-(3,4-dichloro-6-methylphenyl)-2-pyrazoline, 1'-<4-{N-[3-(N,N,N-trimethylammonio)propyl]-amidosulfonyl}phenyl>-3-(4-chlorophenyl)-2-pyrazoline methylsulfate, and 1-<4-{2-[1-methyl-2-(N,N-dimethylamino)ethoxy]ethylsulfonyl}phenyl>-3-(4-chloro phenyl-2-pyrazoline methylsulfate.

Oxazoles

Oxazoles are a class of compounds having the following base structure:

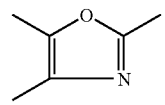

Oxazoles useful in the present inventions include those having formulae (24), (25), (26) and (27):

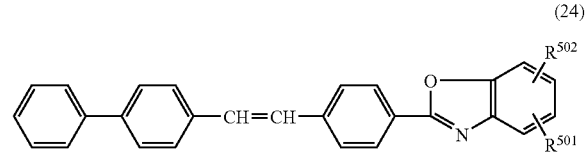
(24)

wherein $R^{501}$ and $R^{502}$, independently, are H, Cl, $C_1$-$C_{30}$alkyl or $SO_2$—$C_1$-$C_{30}$-alkyl, wherein the compound has a trans-coplanar orientation or cis-coplanar orientation; preferably $R^{501}$ is 4-$CH_3$ and $R^{502}$ is 2-$CH_3$ wherein the compound has a trans-coplanar orientation;

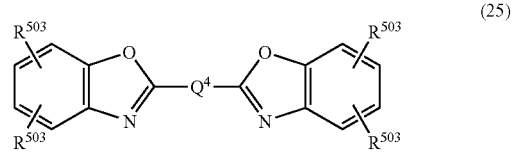
(25)

wherein $R^{503}$, independently, is H, $C(CH_3)_3$, $C(CH_3)_2$-phenyl, $C_1$-$C_{30}$alkyl or COO—$C_1$-$C_{30}$alkyl, preferably H and $Q^4$ is —CH=CH—;

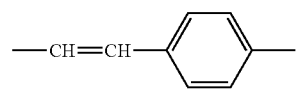

-continued

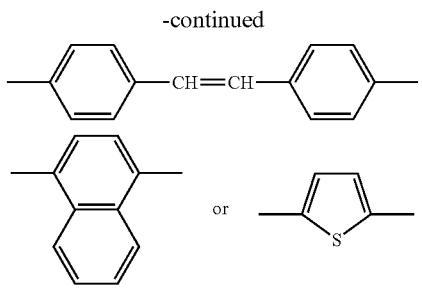

preferably

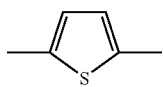

or one group $R^{503}$ in each ring is 2-methyl and the other $R^{503}$ is H and $Q^4$ is —CH=CH—; or one group $R^{503}$ in each ring is 2-C(CH$_3$)$_3$ and the other $R^{503}$ is H; wherein the compound has a trans-coplanar orientation or cis-coplanar orientation, preferably a trans-coplanar orientation;

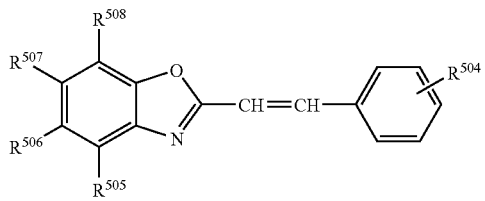

(26)

wherein $R^{504}$ is CN, Cl, COO—C$_1$-C$_{30}$alkyl or phenyl; $R^{505}$ and $R^{506}$ are the atoms required to form a fused benzene ring or $R^{506}$ and $R^{508}$, independently, are H or C$_1$-C$_{30}$alkyl; and $R^{507}$ is H, C$_1$-C$_{30}$alkyl or phenyl; wherein the compound has a trans-coplanar orientation or cis-coplanar orientation; preferably $R^{504}$ is a 4-phenyl group and each of $R^{505}$ to $R^{508}$ is H; wherein the compound has a trans-coplanar orientation; and

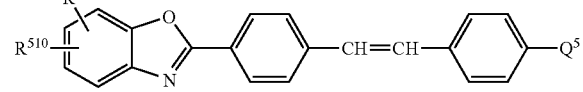

(27)

wherein $R^{509}$ denotes H, Cl, alkyl with 1 to 30 carbon atoms, cyclohexyl, phenylalkyl with 1 to 3 carbon atoms in the alkyl part, phenyl or alkoxy with 1 to 30 carbon atoms, $R^{510}$ denotes H or alkyl with 1 to 30 carbon atoms, and $Q^5$ denotes a radical;

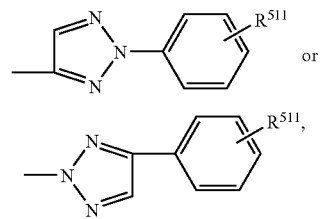

wherein $R^{511}$ represents H, alkyl with 1 to 30 carbon atoms, alkoxy with 1 to 30 carbon atoms, Cl, carbalkoxy with 1 to 30 carbon atoms, unsubstituted sulfamoyl or sulfamoyl which is monosubstituted or disubstituted by alkyl or hydroxyalkyl with 1 to 30 carbon atoms or represents alkylsulfonyl with 1 to 30 carbon atoms; wherein the compound has a trans-coplanar orientation or cis-coplanar orientation, preferably a trans-coplanar orientation.

Suitable oxazoles include 4,4'-bis(5-methylbenzoxazol-2-yl)stilbene, and 2-(4-methoxycarbonylstyryl)benzoxazole.

Pyrenes

Pyrenes useful in the present invention include those having formulae (28) and (29):

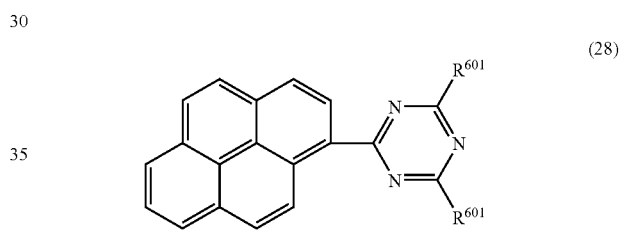

(28)

wherein each $R^{601}$, independently, is C$_1$-C$_{30}$alkoxy; preferably methoxy; and

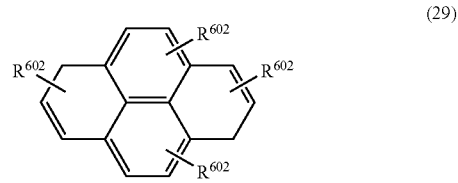

(29)

wherein each $R^{602}$, independently, is H, OH, or SO$_3$M, wherein M is as previously defined, sulfonated phenylamino, or anilino.

Suitable pyrenes include 2,4-dimethoxy-6-(1'-pyrenyl)-1,3,5-triazine (C.I. Fluorescent Brightener 179) with tradename Fluolite XMF, 8-hydroxy-1,3,6-pyrenetrisulfonic acid (D&C Green No. 8), and 3-hydroxy-5,8,10-trisulphanilic pyrene.

Porphyrins

Porphyrins useful in the present invention include those having formulae (30), (31), and (32):

(30)

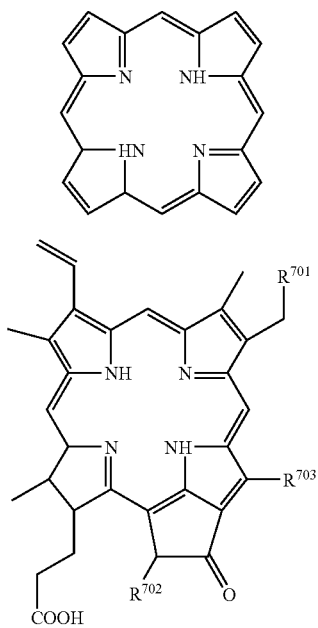

(31)

wherein $R^{701}$ is $CH_3$ or CHO, —$R^{702}$ is H or $COOC_1$-$C_{30}$ alkyl, and $R^{703}$ is H or an alkyl group having 1 to 30 carbons; and (32)

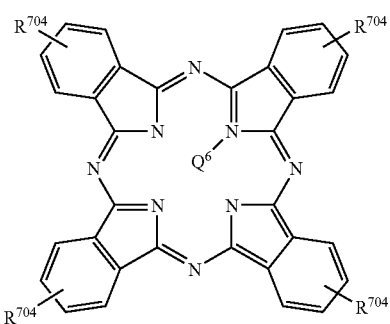

wherein each $R^{704}$, independently, is H, $SO_3M$, COOM, $OSO_3M$, or $OPO(OH)OM$, wherein M is as previously defined, halide, or alkyl of 1 to 30 carbons; and $Q^6$ is Cu, Mg, Fe, Cr, Co, or mixtures thereof with cationic charges.

Suitable porphyrins include porphyrin available from Wako Chemicals and Copper II phthalocyanine available from Wako Chemicals.

Imidazoles

Imidazoles are a class of compounds having the following base structure:

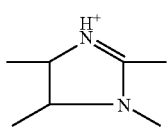

Imidazoles useful in the present invention include those having formulae (33):

(33)

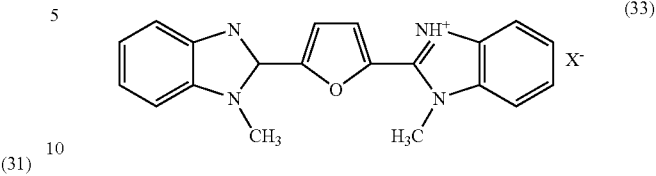

wherein $X^-$ is as previously defined.

Suitable imidazoles include those with tradename of C.I. Fluorescence Brightener 352, or Uvtex AT available from Ciba Speciality Chemical.

Herbal Extract

The compositions of the present invention may further comprise herbal extracts. Herbal extracts useful herein include those which are water soluble and those which are water insoluble. Useful herbal extracts herein include: *Polygonum multiflori* extract, *Houttuynia cordate* extract, *Phellodendron bark* extract, melilot extract, white dead nettle extract, licorice root extract, herbaceous peony extract, soapwort extract, dishcloth gourd extract, cinchona extract, creeping saxifrage extract, *Sophora augustifolia* extract, candock extract, common fennel extract, primrose extract, rose extract, *Rehmannia glutinosa* extract, lemon extract, shikon extract, aloe extract, iris bulb extract, eucalyptus extract, field horsetail extract, sage extract, thyme extract, tea extract, laver extract, cucumber extract, clove extract, raspberry extract, melissa extract, ginseng extract, carrot extract, horse chestnut extract, peach extract, peach leaf extract, mulberry extract, cornflower extract, hamamelis extract, placenta extract, thymus extract, silk extract, algae extract, althea extract, *Angelica dahurica* extract, apple extract, apricot kernel extract, arnica extract, *Artemisia capillaris* extract, astragal extract, balm mint extract, *perilla* extract, birch bark extract, bitter orange peel extract, *Thea sinensis* extract, burdock root extract, burnet extract, butcherbroom extract, *Stephania copharantha* extract, matricaria extract, chrysanthemum flower extract, *citrus unshiu* peel extract, cnidium extract, *coix* seed extract, coltsfoot extract, comfrey leaf extract, *crataegus* extract, evening primrose oil, gambir extract, *ganoderma* extract, gardenia extract, gentian extract, geranium extract, ginkgo extract, grape leaf extract, *crataegus* extract, henna extract, honeysuckle extract, honeysuckle flower extract, hoelen extract, hops extract, horsetail extract, hydrangea extract, *hypericum* extract, isodonis extract, ivy extract, Japanese *angelica* extract, Japanese *coptis* extract, juniper extract, jujube extract, lady's mantle extract, lavender extract, lettuce extract, licorice extract, linden extract, lithospermum extract, loquat extract, *luffa* extract, malloti extract, mallow extract, *calendula* extract, moutan bark extract, mistletoe extract, mukurossi extract, mugwort extract, mulberry root extract, nettle extract, nutmeg extract, orange extract, parsely extract, hydrolyzed conchiorin protein, peony root extract, peppermint extract, philodendron extract, pine cone extract, platycodon extract, polygonatum extract, rehmannia extract, rice bran extract, rhubarb extract, rose fruit extract, rosemary extract, royal jelly extract, safflower extract, saffron crocus extract, *sambucus* extract, *saponaria* extract, Sasa *Sasa albo marginata* extract, *Saxifraga stolonifers* extract, *scutellaria* root extract, *Cortinellus shiitake* extract, lithospermum extract, sophora extract, laurel extract, calamus root extract, *swertia* extract, thyme extract, linden extract, tomato extract, turmeric extract, uncaria extract, watercress extract, logwood extract, grape extract, white lily extract, rose hips extract, wild thyme extract, witch hazel extract, yarrow extract, yeast extract, yucca extract, zanthoxylum extract, and mixtures thereof.

Commercially available extracts useful herein include *Polygonum multiflori* extracts which are water soluble, and available from Institute of Occupational Medicine, CAPM, China National Light Industry, and Maruzen, and other herbal extracts listed above available from Maruzen.

Additional Conditioning Agent

The compositions of the present invention may further comprise an additional conditioning agent selected from the group consisting of high melting point compounds, cationic surfactants, high molecular weight ester oils, cationic polymers, additional oily compounds, and mixtures thereof. Additional conditioning agents are selected according to the compatibility with other components, and the desired characteristic of the product. For example, components of cationic nature will be included in an amount which would not cause separation in view of the essential components of anionic and/or amphoteric nature. The additional conditioning agents herein are preferably used at levels by weight of the composition of from about 0.01% to about 10%.

High Melting Point Compound

The high melting point compound useful herein have a melting point of at least about 25° C. selected from the group consisting of fatty alcohols, fatty acids, fatty alcohol derivatives, fatty acid derivatives, hydrocarbons, steroids, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than about 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

It is believed that these high melting point compounds cover the hair surface and reduce friction, thereby resulting in providing smooth feel on the hair and ease of combing.

The fatty alcohols useful herein are those having from about 14 to about 30 carbon atoms, preferably from about 16 to about 22 carbon atoms. These fatty alcohols can be straight or branched chain alcohols and can be saturated or unsaturated. Nonlimiting examples of fatty alcohols include, cetyl alcohol, stearyl alcohol, behenyl alcohol, and mixtures thereof.

The fatty acids useful herein are those having from about 10 to about 30 carbon atoms, preferably from about 12 to about 22 carbon atoms, and more preferably from about 16 to about 22 carbon atoms. These fatty acids can be straight or branched chain acids and can be saturated or unsaturated. Also included are diacids, triacids, and other multiple acids which meet the requirements herein. Also included herein are salts of these fatty acids. Nonlimiting examples of fatty acids include lauric acid, palmitic acid, stearic acid, behenic acid, sebacic acid, and mixtures thereof.

The fatty alcohol derivatives and fatty acid derivatives useful herein include alkyl ethers of fatty alcohols, alkoxylated fatty alcohols, alkyl ethers of alkoxylated fatty alcohols, esters of fatty alcohols, fatty acid esters of compounds having esterifiable hydroxy groups, hydroxy-substituted fatty acids, and mixtures thereof. Nonlimiting examples of fatty alcohol derivatives and fatty acid derivatives include materials such as methyl stearyl ether; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; $C_1$-$C_{30}$ alkyl ethers of the ceteth, steareth, and ceteareth compounds just described; polyoxyethylene ethers of behenyl alcohol; ethyl stearate, cetyl stearate, cetyl palmitate, stearyl stearate, myristyl myristate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, glyceryl monostearate, glyceryl distearate, glyceryl tristearate, and mixtures thereof.

Hydrocarbons useful herein include compounds having at least about 20 carbons.

Steroids useful herein include compounds such as cholesterol.

High melting point compounds of a single compound of high purity are preferred. Single compounds of pure fatty alcohols selected from the group of pure cetyl alcohol, stearyl alcohol, and behenyl alcohol are highly preferred. By "pure" herein, what is meant is that the compound has a purity of at least about 90%, preferably at least about 95%. These single compounds of high purity provide good rinsability from the hair when the consumer rinses off the composition.

Commercially available high melting point compounds useful herein include: cetyl alcohol, stearyl alcohol, and behenyl alcohol having tradenames KONOL series available from Shin Nihon Rika (Osaka, Japan), and NAA series available from NOF (Tokyo, Japan); pure behenyl alcohol having tradename 1-DOCOSANOL available from WAKO (Osaka, Japan), various fatty acids having tradenames NEO-FAT available from Akzo (Chicago Ill., USA), HYSTRENE available from Witco Corp. (Dublin Ohio, USA), and DERMA available from Vevy (Genova, Italy); and cholesterol having tradename NIKKOL AGUASOME LA available from Nikko.

Cationic Surfactant

Among the cationic surfactants useful herein are those corresponding to the general formula (I):

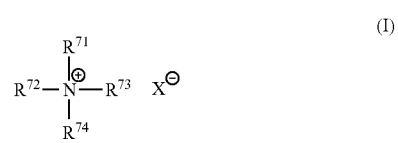

(I)

wherein at least one of $R^{71}$, $R^{72}$, $R^{73}$ and $R^{74}$ is selected from an aliphatic group of from 8 to 30 carbon atoms or an aromatic, alkoxy, polyoxyalkylene, alkylamido, hydroxyalkyl, aryl or alkylaryl group having up to about 22 carbon atoms, the remainder of $R^{71}$, $R^{72}$, $R^{73}$ and $R^{74}$ are independently selected from an aliphatic group of from 1 to about 22 carbon atoms or an aromatic, alkoxy, polyoxyalkylene, alkylamido, hydroxyalkyl, aryl or alkylaryl group having up to about 22 carbon atoms; and X is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The aliphatic groups can contain, in addition to carbon and hydrogen atoms, ether linkages, and other groups such as amino groups. The longer chain aliphatic groups, e.g., those of about 12 carbons, or higher, can be saturated or unsaturated. Preferred is when $R^{71}$, $R^{72}$, $R^{73}$ and $R^{74}$ are independently selected from $C_1$ to about $C_{22}$ alkyl. Nonlimiting examples of cationic surfactants useful in the present invention include the materials having the following CTFA designations: quaternium-8, quaternium-14, quaternium-18, quaternium-18 methosulfate, quaternium-24, and mixtures thereof.

Among the cationic surfactants of general formula (I), preferred are those containing in the molecule at least one alkyl chain having at least 16 carbons. Nonlimiting examples of such preferred cationic surfactants include: behenyl trimethyl ammonium chloride available, for example, with tradename INCROQUAT TMC-80 from Croda and ECONOL TM22 from Sanyo Kasei; cetyl trimethyl ammonium chloride available, for example, with tradename CA-2350 from Nikko Chemicals, hydrogenated tallow alkyl trimethyl ammonium chloride, dialkyl (14-18) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, di(behenyl/arachidyl) dimethyl ammonium chloride, dibehenyl dimethyl ammonium chloride, stearyl dimethyl benzyl ammonium chloride, stearyl propyleneglycol phosphate dimethyl ammonium chloride, stearoyl amidopropyl dimethyl benzyl ammonium chloride, stearoyl amidopropyl dimethyl (myristylacetate) ammonium chloride, and N-(stearoyl colamino formyl methy) pyridinium chloride.

Also preferred are hydrophilically substituted cationic surfactants in which at least one of the substituents contain one or more aromatic, ether, ester, amido, or amino moieties present as substituents or as linkages in the radical chain, wherein at least one of the $R^{71}$-$R^{74}$ radicals contain one or more hydrophilic moieties selected from alkoxy (preferably $C_1$-$C_3$ alkoxy), polyoxyalkylene (preferably $C_1$-$C_3$ polyoxyalkylene), alkylamido, hydroxyalkyl, alkylester, and combinations thereof. Preferably, the hydrophilically substituted cationic conditioning surfactant contains from 2 to about 10 nonionic hydrophile moieties located within the above stated ranges. Preferred hydrophilically substituted cationic surfactants include those of the formula (II) through (VIII) below:

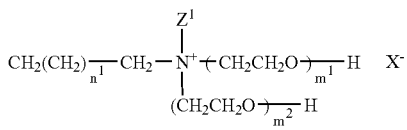

(II)

wherein $n^1$ is from 8 to about 28, $m^1+m^2$ is from 2 to about 40, $Z^1$ is a short chain alkyl, preferably a $C_1$-$C_3$ alkyl, more preferably methyl, or $(CH_2CH_2O)_{m3}H$ wherein $m^1+m^2+m^3$ is up to 60, and X is a salt forming anion as defined above;

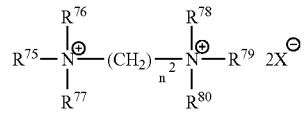

(III)

wherein $n^2$ is 1 to 5, one or more of $R^{75}$, $R^{76}$, and $R^{77}$ are independently an $C_1$-$C_{30}$ alkyl, the remainder are $CH_2CH_2OH$, one or two of $R^{78}$, $R^{79}$, and $R^{80}$ are independently an $C_1$-$C_{30}$ alkyl, and remainder are $CH_2CH_2OH$, and X is a salt forming anion as mentioned above;

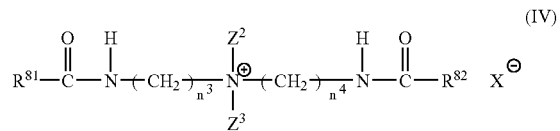

(IV)

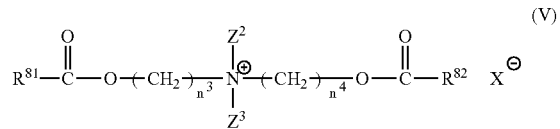

(V)

wherein, independently for formulae (IV) and (V), $Z^2$ is an alkyl, preferably $C_1$-$C_3$ alkyl, more preferably methyl, and $Z^3$ is a short chain hydroxyalkyl, preferably hydroxymethyl or hydroxyethyl, $n^3$ and $n^4$ independently are integers from 2 to 4, inclusive, preferably from 2 to 3, inclusive, more preferably 2, $R^{81}$ and $R^{82}$ independently, are substituted or unsubstituted hydrocarbyls, $C_{12}$-$C_{20}$ alkyl or alkenyl, and X is a salt forming anion as defined above;

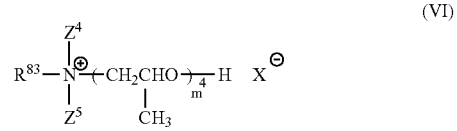

(VI)

wherein $R^{83}$ is a hydrocarbyl, preferably a $C_1$-$C_3$ alkyl, more preferably methyl, $Z^4$ and $Z^5$ are, independently, short chain hydrocarbyls, preferably $C_2$-$C_4$ alkyl or alkenyl, more preferably ethyl, $m^4$ is from 2 to about 40, preferably from about 7 to about 30, and X is a salt forming anion as defined above;

(VII)

wherein $R^{54}$ and $R^{85}$, independently, are $C_1$-$C_3$ alkyl, preferably methyl, $Z^6$ is a $C_{12}$-$C_{22}$ hydrocarbyl, alkyl carboxy or alkylamido, and A is a protein, preferably a collagen, keratin, milk protein, silk, soy protein, wheat protein, or hydrolyzed forms thereof; and X is a salt forming anion as defined above;

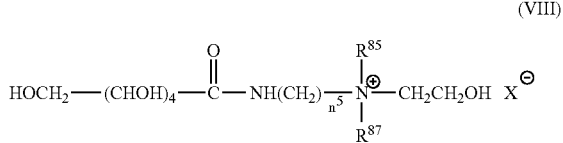

(VIII)

wherein $n^5$ is 2 or 3, $R^{85}$ and $R^{87}$, independently are $C_1$-$C_3$ hydrocarbyls preferably methyl, and X is a salt forming anion as defined above. Nonlimiting examples of hydrophilically substituted cationic surfactants useful in the present invention include the materials having the following CTFA designations: quaternium-16, quaternium-26, quaternium-27, quaternium-30, quaternium-33, quaternium-43, quaternium-52, quaternium-53, quaternium-56, quaternium-60, quaternium-61, quaternium-62, quaternium-70, quaternium-71, quaternium-72, quaternium-75, quaternium-76 hydrolyzed collagen, quaternium-77, quaternium-78, quaternium-79 hydrolyzed collagen, quaternium-79 hydrolyzed keratin, quaternium-79 hydrolyzed milk protein, quaternium-79 hydrolyzed silk, quaternium-79 hydrolyzed soy protein, and quaternium-79 hydrolyzed wheat protein, quaternium-80, quaternium-81, quaternium-82, quaternium-83, quaternium-84, and mixtures thereof.

Highly preferred hydrophilically substituted cationic surfactants include dialkylamido ethyl hydroxyethylmonium salt, dialkylamidoethyl dimonium salt, dialkyloyl ethyl hydroxyethylmonium salt, dialkyloyl ethyldimonium salt, and mixtures thereof; for example, commercially available under the following tradenames; VARISOFT 110, VARISOFT 222, VARIQUAT K1215 and VARIQUAT 638 from Witco Chemical, MACKPRO KLP, MACKPRO WLW, MACKPRO MLP, MACKPRO NSP, MACKPRO NLW, MACKPRO WWP, MACKPRO NLP, MACKPRO SLP from McIntyre, ETHOQUAD 18/25, ETHOQUAD O/12PG, ETHOQUAD C/25, ETHOQUAD S/25, and ETHODUOQUAD from Akzo, DEHYQUAT SP from Henkel, and ATLAS G265 from ICI Americas.

Amines are suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Also useful are dimethylstearamine, dimethylsoyamine, soyamine, myristylamine, tridecylamine, ethylstearylamine, N-tallowpropane diamine, ethoxylated (with 5 moles of ethylene oxide) stearylamine, dihydroxyethylstearylamine, and arachidylbehenylamine. Useful amines in the present invention are disclosed in U.S. Pat. No. 4,275,055, Nachtigal, et al.

These amines can also be used in combination with acids such as $l$-glutamic acid, lactic acid, hydrochloric acid, malic acid, succinic acid, acetic acid, fumaric acid, tartaric acid, citric acid, $l$-glutamic hydrochloride, maleic acid, and mixtures thereof; more preferably $l$-glutamic acid, lactic acid, citric acid. The amines herein are preferably partially neutralized with any of the acids at a molar ratio of the amine to the acid of from about 1:0.3 to about 1:2, more preferably from about 1:0.4 to about 1:1.

High Molecular Weight Ester Oils

High molecular weight ester oils are useful herein. The high molecular weight ester oils useful herein are those which are water insoluble, have a molecular weight of at least about 500, preferably at least about 800, and are in liquid form at 25° C. Useful high molecular weight ester oils herein include pentaethylritol ester oils, trimethylol ester oils, poly α-olefin oils, citrate ester oils, glyceryl ester oils, and mixtures thereof. As used herein, the term "water insoluble" means the compound is substantially not soluble in water at 25° C.; when the compound is mixed with water at a concentration by weight of above 1.0%, preferably at above 0.5%, the compound is temporarily dispersed to form an unstable colloid in water, then is quickly separated from water into two phases.

The high molecular weight ester oil herein provides conditioning benefits such as moisturized feel, smooth feel, and manageability control to the hair when the hair is dried, yet not leave the hair feeling greasy. It is believed that water insoluble oily material in general are capable of being deposited on the hair. Without being bound by theory, it is believed that, because of its bulkiness, the high molecular weight ester oil covers the surface of the hair and, as a result, the high molecular weight ester oil reduces hair friction to deliver smoothness and manageability control to the hair. It is also believed that, because it has some hydrophilic groups, the high molecular weight ester oil provides moisturized feel, yet, because it is liquid, does not leave the hair feeling greasy. The high molecular weight ester oil is chemically stable under normal use and storage conditions.

Pentaerythritol ester oils useful herein are those having the following formula:

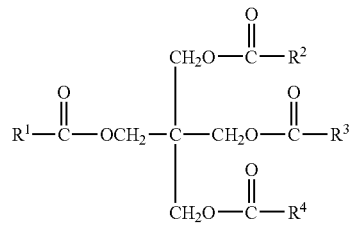

wherein $R^1$, $R^2$, $R^3$, and $R^4$, independently, are branched, straight, saturated, or unsaturated alkyl, aryl, and alkylaryl groups having from 1 to about 30 carbons. Preferably, $R^1$, $R^2$, $R^3$, and $R^4$, independently, are branched, straight, saturated, or unsaturated alkyl groups having from about 8 to about 22 carbons. More preferably, $R^1$, $R^2$, $R^3$ and $R^4$ are defined so that the molecular weight of the compound is from about 800 to about 1200.

Trimethylol ester oils useful herein are those having the following formula:

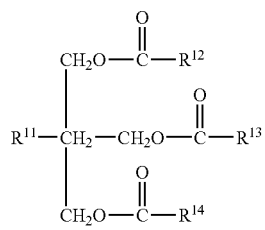

wherein $R^{11}$ is an alkyl group having from 1 to about 30 carbons, and $R^{12}$, $R^{13}$, and $R^{14}$, independently, are branched, straight, saturated, or unsaturated alkyl, aryl, and alkylaryl groups having from 1 to about 30 carbons. Preferably, $R^{11}$ is ethyl and $R^{12}$, $R^{13}$, and $R^{14}$, independently, are branched, straight, saturated, or unsaturated alkyl groups having from 8 to about 22 carbons. More preferably, $R^{11}$, $R^{12}$, $R^{13}$ and $R^{14}$ are defined so that the molecular weight of the compound is from about 800 to about 1200.

Poly α-olefin oils useful herein are those having the following formula and having a viscosity of from about 1 to about 35,000 cst, a molecular weight of from about 200 to about 60,000, and a polydispersity of no more than about 3;

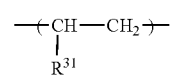

wherein $R^{31}$ is an alkyl having from about 4 to 14 carbons, preferably 4 to 10 carbons. Poly α-olefin oils having a molecular weight of at least about 800 are useful herein. Such high molecular weight poly α-olefin oils are believed to provide long lasting moisturized feel to the hair. Poly α-olefin oils having a molecular weight of less than about 800 are useful herein. Such low molecular weight poly α-olefin oils are believed to provide a smooth, light, clean feel to the hair.

Citrate ester oils useful herein are those having a molecular weight of at least about 500 having the following formula:

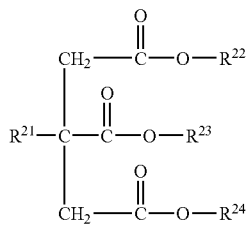

wherein $R^{21}$ is OH or $CH_3COO$, and $R^{22}$, $R^{23}$, and $R^{24}$, independently, are branched, straight, saturated, or unsaturated alkyl, aryl, and alkylaryl groups having from 1 to about 30 carbons. Preferably, $R^{21}$ is OH, and $R^{22}$, $R^{23}$, and $R^{24}$, independently, are branched, straight, saturated, or unsaturated alkyl, aryl, and alkylaryl groups having from 8 to about 22 carbons. More preferably, $R^{21}$, $R^{22}$, $R^{23}$ and $R^{24}$ are defined so that the molecular weight of the compound is at least about 800.

Glyceryl ester oils useful herein are those having a molecular weight of at least about 500 and having the following formula:

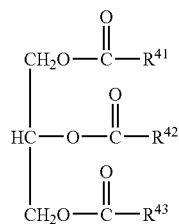

wherein $R^{41}$, $R^{42}$, and $R^{43}$, independently, are branched, straight, saturated, or unsaturated alkyl, aryl, and alkylaryl groups having from 1 to about 30 carbons. Preferably, $R^{41}$, $R^{42}$, and $R^{43}$, independently, are branched, straight, saturated, or unsaturated alkyl, aryl, and alkylaryl groups having from 8 to about 22 carbons. More preferably, $R^{41}$, $R^{42}$, and $R^{43}$ are defined so that the molecular weight of the compound is at least about 800.

Particularly useful pentaerythritol ester oils and trimethylol ester oils herein include pentaerythritol tetraisostearate, pentaerythritol tetraoleate, trimethylolpropane triisostearate, trimethylolpropane trioleate, and mixtures thereof. Such compounds are available from Kokyo Alcohol with tradenames KAKPTI, KAKTTI, and Shin-nihon Rika with tradenames PTO, ENUJERUBU TP3SO.

Particularly useful poly α-olefin oils herein include polydecenes with tradenames PURESYN 6 having a number average molecular weight of about 500 and PURESYN 100 having a number average molecular weight of about 3000 and PURESYN 300 having a number average molecular weight of about 6000 available from Mobil Chemical Co.

Particularly useful citrate ester oils herein include triisocetyl citrate with tradename CITMOL 316 available from Bernel, triisostearyl citrate with tradename PELEMOL TISC available from Phoenix, and trioctyldodecyl citrate with tradename CITMOL 320 available from Bernel.

Particularly useful glyceryl ester oils herein include triisostearin with tradename SUN ESPOL G-318 available from Taiyo Kagaku, triolein with tradename CITHROL GTO available from Croda Surfactants Ltd., trilinolein with tradename EFADERMA-F available from Vevy, or tradename EFA-GLYCERIDES from Brooks.

Cationic Polymers

Cationic polymers are useful herein. As used herein, the term "polymer" shall include materials whether made by polymerization of one type of monomer or made by two (i.e., copolymers) or more types of monomers.

Preferably, the cationic polymer is a water soluble cationic polymer. By "water soluble" cationic polymer, what is meant is a polymer which is sufficiently soluble in water to form a substantially clear solution to the naked eye at a concentration of 0.1% in water (distilled or equivalent) at 25° C. The preferred polymer will be sufficiently soluble to form a substantially clear solution at 0.5% concentration, more preferably at 1.0% concentration.

The cationic polymers hereof will generally have a weight average molecular weight which is at least about 5,000, typically at least about 10,000, and is less than about 10 million. Preferably, the molecular weight is from about 100,000 to about 2 million. The cationic polymers will generally have cationic nitrogen-containing moieties such as quaternary ammonium or cationic amino moieties, and mixtures thereof.

Any anionic counterions can be utilized for the cationic polymers so long as the water solubility criteria is met. Suitable counterions include halides (e.g., Cl, Br, I, or F, preferably Cl, Br, or I), sulfate, and methylsulfate. Others can also be used, as this list is not exclusive.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in the CTFA Cosmetic Ingredient Dictionary, 3rd edition, edited by Estrin, Crosley, and Haynes, (The Cosmetic, Toiletry, and Fragrance Association, Inc., Washington, D.C., 1982).

The cationic amines can be primary, secondary, or tertiary amines, depending upon the particular species and the pH of the composition. In general, secondary and tertiary amines, especially tertiary amines, are preferred.

Amine-substituted vinyl monomers can be polymerized in the amine form, and then optionally can be converted to ammonium by a quaternization reaction. Amines can also be similarly quaternized subsequent to formation of the polymer. For example, tertiary amine functionalities can be quaternized by reaction with a salt of the formula $R^{88}X$ wherein $R^{88}$ is a short chain alkyl, preferably a $C_1$-$C_7$ alkyl, more preferably a $C_1$-$C_3$ alkyl, and X is a salt forming anion as defined above.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$-$C_3$ alkyls, more preferably $C_1$ and $C_2$ alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$-$C_7$ hydrocarbyls, more preferably $C_1$-$C_3$, alkyls.

The cationic polymers hereof can comprise mixtures of monomer units derived from amine- and/or quaternary ammonium-substituted monomer and/or compatible spacer monomers.

Suitable cationic hair conditioning polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., USA) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from Gaf Corporation (Wayne, N.J., USA) under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, respectively; and mineral acid salts of amino-alkyl esters of homo- and co-polymers of unsaturated carboxylic acids having from 3 to 5 carbon atoms, as described in U.S. Pat. No. 4,009,256.

Other cationic polymers that can be used include polysaccharide polymers, such as cationic cellulose derivatives and cationic starch derivatives.

Cationic polysaccharide polymer materials suitable for use herein include those of the formula:

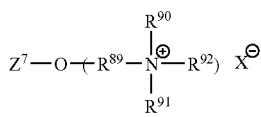

wherein: $Z^7$ is an anhydroglucose residual group, such as a starch or cellulose anhydroglucose residual, $R^{89}$ is an alkylene oxyalkylene, polyoxyalkylene, or hydroxyalkylene group, or combination thereof, $R^{90}$, $R^{91}$, and $R^{92}$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^{90}$, $R^{91}$ and $R^{92}$) preferably being about 20 or less, and X is as previously described.

Cationic cellulose is available from Amerchol Corp. (Edison, N.J., USA) in their Polymer JR® and LR® series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200®.

Other cationic polymers that can be used include cationic guar gum derivatives, such as guar hydroxypropyltrimonium chloride commercially available from Celanese Corp. in their Jaguar R series. Other materials include quaternary nitrogen-containing cellulose ethers as described in U.S. Pat. No. 3,962,418, and copolymers of etherified cellulose and starch as described in U.S. Pat. No. 3,958,581.

Particularly useful cationic polymers herein include Polyquaternium-7, Polyquaternium-10, Polyquaternium-24, and mixtures thereof.

Additional Oily Compounds

Additional oily compounds useful herein include fatty alcohols and their derivatives, fatty acids and their derivatives, and hydrocarbons. The additional oily compounds useful herein may be volatile or nonvolatile, and have a melting point of not more than about 25° C. Without being bound by theory, it is believed that, the additional oily compounds may penetrate into the hair to modify the hydroxy bonds of the hair, thereby resulting in providing softness and flexibility to the hair. The additional oily compounds of this section are to be distinguished from the high melting point compounds described above. Nonlimiting examples of the additional oily compounds are found in International Cosmetic Ingredient Dictionary, Fifth Edition, 1993, and CTFA Cosmetic Ingredient Handbook, Second Edition, 1992.

The fatty alcohols useful herein include those having from about 10 to about 30 carbon atoms, preferably from about 12 to about 22 carbon atoms, and more preferably from about 16 to about 22 carbon atoms. These fatty alcohols can be straight or branched chain alcohols and can be saturated or unsaturated alcohols, preferably unsaturated alcohols. Nonlimiting examples of these compounds include oleyl alcohol, palmitoleic alcohol, isostearyl alcohol, isocetyl alcohol, undecanol, octyl dodecanol, octyl decanol, octyl alcohol, caprylic alcohol, decyl alcohol and lauryl alcohol.

The fatty acids useful herein include those having from about 10 to about 30 carbon atoms, preferably from about 12 to about 22 carbon atoms, and more preferably from about 16 to about 22 carbon atoms. These fatty acids can be straight or branched chain acids and can be saturated or unsaturated. Suitable fatty acids include, for example, oleic acid, linoleic acid, isostearic acid, linolenic acid, ethyl linolenic acid, ethyl linolenic acid, arachidonic acid, and ricinolic acid.

The fatty acid derivatives and fatty alcohol derivatives are defined herein to include, for example, esters of fatty alcohols, alkoxylated fatty alcohols, alkyl ethers of fatty alcohols, alkyl ethers of alkoxylated fatty alcohols, and bulky ester oils such as pentaerythritol ester oils, trimethylol ester oils, citrate ester oils, glyceryl ester oils, and mixtures thereof. Nonlimiting examples of fatty acid derivatives and fatty alcohol derivatives, include, for example, methyl linoleate, ethyl linoleate, isopropyl linoleate, isodecyl oleate, isopropyl oleate, ethyl oleate, octyidodecyl oleate, oleyl oleate, decyl oleate, butyl oleate, methyl oleate, octyidodecyl stearate, octyidodecyl isostearate, octyldodecyl isopalmitate, octyl isopelargonate, octyl pelargonate, hexyl isostearate, isopropyl isostearate, isodecyl isononanoate, isopropyl stearate, ethyl stearate, methyl stearate and Oleth-2. Bulky ester oils such as pentaerythritol ester oils, trimethylol ester oils, citrate ester oils and glyceryl ester oils useful herein are those which have a molecular weight of less than about 800, preferably less than about 500.

The hydrocarbons useful herein include straight chain, cyclic, and branched chain hydrocarbons which can be either saturated or unsaturated, so long as they have a melting point of not more than about 25° C. These hydrocarbons have from about 12 to about 40 carbon atoms, preferably from about 12 to about 30 carbon atoms, and preferably from about 12 to about 22 carbon atoms. Also encompassed herein are polymeric hydrocarbons of alkenyl monomers, such as polymers of $C_{2-6}$ alkenyl monomers. These polymers can be straight or branched chain polymers. The straight chain polymers will typically be relatively short in length, having a total number of carbon atoms as described above. The branched chain polymers can have substantially higher chain lengths. The number average molecular weight of such materials can vary widely, but will typically be up to about 500, preferably from about 200 to about 400, and more preferably from about 300 to about 350. Also useful herein are the various grades of mineral oils. Mineral oils are liquid mixtures of hydrocarbons that are obtained from petroleum. Specific examples of suitable hydrocarbon materials include paraffin oil, mineral oil, dodecane, isododecane, hexadecane, isohexadecane, eicosene, isoeicosene, tridecane, tetradecane, polybutene, polyisobutene, and mixtures thereof. Preferred for use herein are hydrocarbons selected from the group consisting of mineral oil, poly α-olefin oils such as isododecane, isohexadecane, polybutene, polyisobutene, and mixtures thereof.

Commercially available fatty alcohols and their derivatives useful herein include: oleyl alcohol with tradename UNJECOL 90BHR available from Shin Nihon Rika, various liquid esters with tradenames SCHERCEMOL series available from Scher, and hexyl isostearate with a tradename HIS and isopropryl isostearate having a tradename ZPIS available from Kokyu Alcohol. Commercially available bulky ester oils useful herein include: trimethylolpropane tricaprylate/tricaprate with tradename MOBIL ESTER P43 from Mobil Chemical Co. Commercially available hydrocarbons useful herein include isododecane, isohexadeance, and isoeicosone with tradenames PERMETHYL 99A, PERMETHYL 101A, and PERMETHYL 1082, available from Presperse (South Plainfield N.J., USA), a copolymer of isobutene and normal butene with tradenames INDOPOL H-100 available from Amoco Chemicals (Chicago Ill., and USA), mineral oil with tradename BENOL available from Witco, isoparaffin with tradename ISOPAR from Exxon Chemical Co. (Houston Tex., USA.)

Other Additional Components

The compositions of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: other conditioning agents such as hydrolysed collagen with tradename Peptein 2000 available from Hormel, vitamin E with tradename Emix-d available from Eisai, panthenol available from Roche, panthenyl ethyl ether available from Roche, hydrolysed keratin, proteins, plant extracts, and nutrients; hair-fixative polymers such as amphoteric fixative polymers, cationic fixative polymers, anionic fixative polymers, nonionic fixative polymers, and silicone grafted copolymers; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; hair oxidizing (bleaching) agents, such as hydrogen peroxide, perborate and persulfate salts; hair reducing agents such as the thioglycolates; perfumes; and sequestering agents, such as disodium ethylenediamine tetra-acetate; ultraviolet and infrared screening and absorbing agents such as octyl salicylate, anti-dandruff agents such as zinc pyrithione; and mixtures thereof.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Ingredients are identified by chemical or CTFA name, or otherwise defined below.

| Compositions | Ex. 1 | Ex. 2 | Ex. 3 | Ex. 4 | Ex. 5 | Ex. 6 |
|---|---|---|---|---|---|---|
| Acrylic acid/alkyl acrylate copolymer 1 *1 | 0.3 | 0.5 | — | 0.5 | 0.3 | — |
| Acrylic acid/alkyl acrylate copolymer 2 *2 | — | — | 0.5 | — | — | 0.3 |
| Visible particle 1 *20 | 0.1 | — | — | — | — | 0.2 |
| Visible particle 2 *21 | — | 0.2 | — | 0.5 | — | 0.2 |
| Visible particle 5 *34 | — | — | 1.0 | — | 0.5 | — |
| Triethanolamine *30 | 0.5 | 0.6 | 0.7 | 0.6 | 0.5 | 0.5 |
| Polyquaternium-39 *3 | 0.2 | 0.1 | 0.1 | 0.1 | 0.5 | 1.0 |
| Carbomer 1 *6 | 0.1 | — | 0.2 | — | 0.1 | — |
| Carbomer 2 *7 | — | — | — | 0.5 | — | 0.3 |
| Acrylates/Steareth-20 Methacrylate Copolymer *10 | — | — | — | — | — | 0.2 |
| Dimethicone and Dimethiconol *11 | 1.0 | 1.0 | — | — | — | — |
| Cyclomethicone/Dimethiconol *12 | — | — | — | 3.0 | — | — |
| Cyclomethicone/Dimethicone *13 | — | — | 3.0 | — | — | — |
| Cyclomethicone *14 | — | — | 2.0 | — | — | — |
| Propylene Glycol | 2.0 | 4.0 | — | — | — | 2.0 |
| Hexylene Glycol *16 | — | — | — | — | 2.0 | — |
| Polyethylene Glycol 200 *17 | — | — | 2.0 | 4.0 | — | 1.0 |
| 2,4-dimethoxy-6-(1'pyrenyl)-1,3,5-triazine *26 | — | — | — | — | — | 1.0 |
| Porphyrin *27 | — | — | — | — | 1.0 | — |
| *Polygonum multiflori* extract *24 | 0.1 | 0.1 | — | — | — | — |
| Vitamin E *35 | — | — | — | — | 0.05 | — |
| Pantenol *36 | — | — | — | — | — | 0.1 |
| Benzophenone-4 *18 | 0.1 | — | 0.1 | 0.1 | 0.1 | 0.1 |
| Octyl Methoxycinnamate *19 | — | 0.1 | — | — | — | 0.2 |
| Methyl Paraben | 0.2 | 0.2 | 0.2 | 0.2 | 0.2 | 0.2 |
| Phenoxyethanol | 0.3 | 0.3 | 0.3 | 0.3 | 0.3 | 0.3 |
| Disodium EDTA | 0.1 | 0.1 | 0.1 | 0.1 | 0.1 | 0.1 |
| Perfume solution | 0.1 | 0.1 | 0.1 | 0.1 | 0.1 | 0.1 |
| Deionized Water | q.s. to 100% | | | | | |

| | Ex. 7 | Ex. 8 | Ex. 9 | Ex. 10 | Ex. 11 | Ex. 12 |
|---|---|---|---|---|---|---|
| Acrylic acid/alkyl acrylate copolymer 1 *1 | 0.5 | — | 1.0 | — | — | 0.2 |
| Acrylic acid/alkyl acrylate copolymer 2 *2 | — | 0.5 | — | 1.0 | 0.3 | 0.3 |
| Triethanolamine *30 | 0.6 | 0.6 | 0.8 | 0.8 | 0.3 | 0.6 |
| Visible particles 3 *32 | 0.1 | — | — | 0.5 | — | — |
| Visible particles 4 *33 | — | 0.1 | — | — | 0.5 | — |
| Visible particles 5 *35 | — | — | 0.5 | — | — | 0.2 |
| Cetyl hydroxyethylcellulose *8 | — | — | — | 0.2 | — | — |
| Hydroxyethylcellulose *9 | — | — | — | — | 0.1 | — |
| Polyquaternium-39 *3 | 0.2 | 0 | — | 0.5 | 1.0 | — |
| Polyquaternium-47 *4 | — | 0.2 | — | — | — | 2.0 |
| Polyquaternium-22 *5 | — | — | 0.1 | — | — | — |
| PEG-2M *22 | 0.1 | — | — | — | — | — |
| Polyethylene Glycol 200 *17 | — | — | — | 4.0 | — | — |
| Propylene Glycol | 4.0 | — | — | — | 2.0 | — |

-continued

| Compositions | | | | | | |
|---|---|---|---|---|---|---|
| Hexylene Glycol *16 | — | 2.0 | — | — | — | — |
| Alkyl Silicone *14 | — | — | — | — | — | 2.0 |
| Alkyl Silicone Emulsion *15 | — | — | — | — | 2.0 | — |
| Behenyl trimethyl ammonium chloride *28 | — | 0.2 | — | — | — | — |
| Polyquaternium-24 *29 | — | — | 0.1 | — | — | — |
| Pentaerythritol Tetraoleate *31 | — | — | — | 0.2 | — | — |
| Aloe Extract *23 | — | — | — | — | — | 1.0 |
| Polygonum multiflori extract *24 | — | 0.2 | — | 0.2 | — | — |
| Ginseng *25 | — | — | 0.1 | — | — | — |
| Benzophenone-4 *18 | 0.5 | — | — | 0.2 | 1.0 | 0.1 |
| Octyl Methoxycinnamate *19 | — | 1.0 | 0.2 | 0.2 | — | — |
| Methyl Paraben | 0.2 | 0.2 | 0.2 | 0.2 | 0.2 | 0.2 |
| Phenoxyethanol | 0.1 | 0.1 | 0.1 | 0.1 | 0.1 | 0.1 |
| Disodium EDTA | 0.1 | 0.1 | 0.1 | 0.1 | 0.1 | 0.1 |
| Perfume solution | 0.1 | 0.1 | 0.1 | 0.1 | 0.1 | 0.1 |
| Deionized Water | q.s. to 100% | | | | | |

Definitions of Components
*1 Acrylic acid/alkyl acrylate copolymer 1: PEMULEN TR-1 available from B. F. Goodrich
*2 Acrylic acid/alkyl acrylate copolymer 2: PEMULEN TR-2 available from B. F. Goodrich
*3 Polyquaternium-39: Merquat Plus 3330 available from Calgon
*4 Polyquaternium-47: Merquat 2001 available from Calgon
*5 Polyquaternium-22: Merquat 280 available from Calgon
*6 Carbomer: 1Carbopol 981 available from B. F. Goodrich
*7 Carbomer 2: Carbopol Ultrez 10 available from B. F. Goodrich
*8 Cetyl hydroxyethylcellulose: Polysurf 67 available from Aqualon
*9 Hydroxyethylcellulose: Amercell polymer HM-1500 available from Amerchol
*10 Acrylates/Steareth-20 Methacrylate Copolymer: Acrysol 22 available from Rohm and Hass
*11 Dimethicone and Dimethiconol: DCQ2-1403 available from Dow Corning
*12 Cycomethicone/Dimethiconol: DCQ2-1401 available from Dow Corning
*13 Cyclomethicone/Dimethicone: Gum/Cyclomethicone blend available from Shin-Etsu
*14 Cyclomethicone: DC345 available from Dow Corning
*15 Alkyl Silicone Emulsion: Alkyl grafted copolymer silicone emulsion DC2-2845 from Dow Corning
*16 Hexylene Glycol: Hexylene glycol available from Mitsui Toatsu
*17 Polyethylen Glycol 200: Carbowax PEG200 available from Union Carbide
*18 Benzophenone-4: Uvnul MS-40 available from BASF
*19 Octyl Methoxycinnamate: Parasol MCX available from Roche
*20 Visible particles 1: Unispheres AGE-527 available from Induchem AG
*21 Visible particles 2: Unispheres YE-501 available from Induchem.AG
*22 PEG-2M: Polyox PEG 2M available from Amerchol.
*23 Aloe Extract: Aloe Extract Vera obtained from Ichimaru Farcos.
*24 Polygonum multiflori extract: Polygonum multiflori extract obtained form Occupational Medicine, CAPM.
*25 Ginseng: Ginseng available from Occupational Medicine, CAPM
*26 2,4-dimethoxy-6-(1'pyrenyl)-1,3,5-triazine: 2,4-dimethoxy-6-(1'pyrenyl)-1,3,5-triazine available from Ciba Geigy
*27 Porphyrin: Porphyrin available from Wako Chemicals
*28 Behenyl trimethyl ammonium chloride: INCROQUAT TMC-80 available from Croda
*29 Polyquaternium-24: Polymer LM-200 available from Amerchol
*30 Triethanolamine: Triethanolamine available from Nippon Shokubai
*31 Pentaerythritol Tetraoleate: Pentaerythritol Tetraoleate Available from Shinnihon Rika
*32 Visible particles 3: Unicerin C-30 available from Induchem AG
*33 Visible particles 4: Unisphers UEA-509 available from Induchem AG
*34 Visible particles 5: Confetti Dermal Essentials series: available from United Guardian Inc.
*35 Vitamin E: Emix-d Available from Eisai
*36 Panthenol: Panthenol Available from Roche Method of Preparation The polymeric materials such as the carboxylic acid/alkyl carboxylate copolymer, amphoteric conditioning polymer, and additional viscosity modifier, if present, are dispersed in water at room temperature, mixed by vigorous agitation, and then heated to about 50° C. The obtained mixture is cooled to below 4000, and then the neutralizing agent is added to the mixture. A triblender can be used if necessary to disperse the polymeric materials.

After neutralizing, the remaining components are added to the mixture. If cationic surfactant is included in the formulation, a premix is made by dissolving the cationic surfactant into hot water having a temperature of above 70° C. with agitation and then cooled to below 40° C. The obtained premix is added to the mixture.

Examples 1 through 12 are hair conditioning compositions of the present invention which are particularly useful for leave-on use. These examples have many advantages. For example, they can provide favorable aesthetic benefit, improved conditioning benefits to the hair such as smoothness, softness, and reduction of friction, are easy to apply on the hair, and leave the hair and hands with a clean feeling.

It is understood that the examples and embodiments described herein are for illustrative purposes only and that various modifications or changes in light thereof will be suggested to one skilled in the art without departing from its spirit and scope.

What is claimed is:

1. A leave-on hair conditioning composition comprising:
   (1) an Acrylates/C10-30 Alkyl Acrylate Crosspolymer;
   (2) visible particles which can be detected as individual particles by the naked eye in the composition and which are stable in the composition, wherein the particles have an average diameter of about 300 µm to about 3000 µm;
   (3) an aqueous carrier selected from water and water solutions of lower alcohols;
   (4) a humectant comprising a polyethylene glycol having a molecular weight of up to about 1000, wherein the hair conditioning composition is free of anionic, nonionic, and amphoteric surfactants.

2. The hair conditioning composition according to claim 1 further comprising an amphoteric conditioning polymer.

3. The hair conditioning composition according to claim 1 further comprising a silicone compound.

4. The hair conditioning composition according to claim 1 further comprising a viscosity modifier.

5. The hair conditioning composition according to claim 1 further comprising a UV absorber.

6. The hair conditioning composition according to claim 1 further comprising an optical brightener.

7. The hair conditioning composition according to claim 1 further comprising a herbal extract.

8. The hair conditioning composition according to claim 1 further comprising a conditioning agent.

9. A leave-on hair conditioning composition comprising by weight:
   (1) from about 0.01% to about 10% of an Acrylates/C10-30 Alkyl Acrylate Crosspolymer;
   (2) from about 0.01% to about 5% of visible particles which can be detected as an individual particles by the naked eye in the composition and which are stable in the composition, wherein the particles have an average diameter of about 300 µm to about 3000 µm;
   (3) from about 0.1% to about 20% of a humectant comprising a polyethylene glycol having a molecular weight of up to about 1000;

(4) from about 0.1% to about 60% of a silicone compound;

(5) from about 0.01% to about 10% of an additional a viscosity modifier; and (6) an aqueous carrier selected from water and water solutions of lower alcohols; and wherein the hair conditioning composition is free of anionic, nonionic, and amphoteric surfactants.

10. The composition of claim 1 wherein the visible particles have an average diameter of about 300 μm to about 1000 μm.

11. The composition of claim 9 wherein the visible particles have an average diameter of about 300 μm to about 1000 μm.

* * * * *